(12) United States Patent
Mitsunaga et al.

(10) Patent No.: US 9,218,315 B2
(45) Date of Patent: Dec. 22, 2015

(54) X-RAY ANALYSIS APPARATUS

(71) Applicant: RIGAKU CORPORATION, Akishima-shi (JP)

(72) Inventors: Toru Mitsunaga, Hachioji (JP); Keiichi Morikawa, Fuchu (JP); Katsuhiko Inaba, Yokohama (JP)

(73) Assignee: RIGAKU CORPORATION, Akishima-Shi, Tokyo (JP)

( * ) Notice: Subject to any disclaimer, the term of this patent is extended or adjusted under 35 U.S.C. 154(b) by 558 days.

(21) Appl. No.: 13/672,773

(22) Filed: Nov. 9, 2012

(65) Prior Publication Data

US 2013/0138382 A1 May 30, 2013

(30) Foreign Application Priority Data

Nov. 29, 2011 (JP) ................................. 2011-259887
Nov. 29, 2011 (JP) ................................. 2011-259888

(51) Int. Cl.
*G06F 19/00* (2011.01)
*G06F 17/00* (2006.01)
*G01N 23/20* (2006.01)

(52) U.S. Cl.
CPC ................ *G06F 17/00* (2013.01); *G01N 23/20* (2013.01); *G01N 2223/306* (2013.01)

(58) Field of Classification Search
CPC .................... G01N 2223/0568; G01N 23/223; G01N 23/22; G01N 2223/076
See application file for complete search history.

(56) References Cited

U.S. PATENT DOCUMENTS

| | | | | |
|---|---|---|---|---|
| 3,624,395 A * | 11/1971 | Togel et al. | .................... | 378/82 |
| 3,790,792 A * | 2/1974 | Ishijima | .......................... | 378/49 |
| 3,806,726 A * | 4/1974 | Ishijima | .......................... | 378/49 |
| 7,555,391 B2 * | 6/2009 | Gleitman | ......................... | 702/9 |
| 2008/0056452 A1 | 3/2008 | Sasaki et al. | | |

FOREIGN PATENT DOCUMENTS

| | | |
|---|---|---|
| EP | 1895292 A2 | 3/2008 |
| GB | 2290689 A | 1/1996 |
| JP | 05113418 A | 5/1993 |

(Continued)

OTHER PUBLICATIONS

Smits et al. 'An Integrating Weissenberg Apparatus for X-ray analysis', 1950, Acta Cryst, vol. 3, pp. 1-5.*

(Continued)

*Primary Examiner* — Elias Desta
(74) *Attorney, Agent, or Firm* — Buchanan Ingersoll & Rooney PC

(57) ABSTRACT

An X-ray analysis apparatus having a function for enabling a plurality of measurement methods to be implemented, the X-ray analysis apparatus having: a measurement system capable of implementing a plurality of measurement methods; measurement software for implementing, in a selective manner, each of the measurement methods; a material evaluation table for storing information relating to a material that may be measured, and a name of an evaluation performed on the material; an input device for inputting the information relating to the material; a wizard program for performing computation for selecting the name of an evaluation on the basis of the information relating to the material inputted using the input device; and a wizard program for selecting a corresponding measurement method on the basis of the selected name of the evaluation.

9 Claims, 21 Drawing Sheets

(56) References Cited

FOREIGN PATENT DOCUMENTS

| | | |
|---|---|---|
| JP | 06-074923 A | 3/1994 |
| JP | 07282764 A | 10/1995 |
| JP | 11064250 A | 3/1999 |
| JP | 2001-056304 A | 2/2001 |
| JP | 2002-365244 | 12/2002 |
| JP | 2005265502 A | 9/2005 |
| JP | 2006220462 A | 8/2006 |
| JP | 2008-057989 A | 3/2008 |

OTHER PUBLICATIONS

Japanese Office Action Issued Jun. 3, 2015 in related Japanese Patent Application No. 2012-192579 (3 pages).

Japanese Office Action Issued Jun. 10, 2015 in related Japanese Patent Application No. 2012-192637 (3 pages).

* cited by examiner

FIG. 7

0. SELECT MATERIAL FIELD

Smart GUIDE – SELECT MATERIAL FIELD

PLEASE SELECT MATERIAL FIELD

- ⦿ TRANSPARENT CONDUCTIVE FILM
- ○ ORGANIC FILM
- ○ INTERCONNECTING ELECTRODE
- ○ FERROELECTRIC FILM
- ○ MAGNETIC FILM
- ○ SUBSTRATE

← 46a

APPLICATION
APPLICATION
APPLICATION
APPLICATION
APPLICATION
APPLICATION

45

CANCEL  <BACK  NEXT>  END

FIG. 8

1. SELECT MATERIAL

TRANSPARENT CONDUCTIVE FILM (1/5) – SELECT MATERIAL

PLEASE SELECT MATERIAL YOU WISH TO MEASURE

○ ITO FILM
⦿ ZnO FILM
○ SnO₂ FILM
○ OTHER CRYSTAL PHASE [TiO2(tet)rutile ▶]

46b

47a

[CANCEL] [<BACK] [NEXT>] [END]

FIG. 10

2. INPUT SAMPLE INFORMATION

TRANSPARENT CONDUCTIVE FILM (2/5) – INPUT SAMPLE INFORMATION

PLEASE INPUT FILE NAME AND SAMPLE INFORMATION
(CAN BE EDITED AFTER MACRO HAS BEEN CREATED)

SAVE MEASUREMENT DATA

FILE NAME: Default.ras
SAMPLE NAME
MEMO

SAMPLE INFORMATION
SAMPLE THICKNESS (mm): 1.0
SAMPLE WIDTH (mm): 20.0
SAMPLE HEIGHT (mm): 20.0

CANCEL  <BACK  NEXT>  END

FIG. 11
3. SELECT EVALUATION CATEGORY

TRANSPARENT CONDUCTIVE FILM (3/5) – SELECT EVALUATION CATEGORY

PLEASE SELECT CATEGORY TO EVALUATE

TRANSPARENT CONDUCTIVE FILM APPLICATION

- ☐ STUDY FILM THICKNESS/DENSITY/ROUGHNESS — SELECT FILM THICKNESS — DETAILS
- ☐ STUDY CRYSTAL PHASE — SELECT MEASUREMENT METHOD... — DETAILS
- ☐ STUDY CRYSTALLITE SIZE/DEFORMATION — SELECT MEASUREMENT DIRECTION... — DETAILS
- ☐ STUDY LATTICE CONSTANT
- ☐ STUDY DEGREE OF ALIGNMENT — SELECT MEASUREMENT DIRECTION... — DETAILS

← 46c

WHAT IS OBTAINED THROUGH X-RAY DIFFRACTION MEASUREMENT

PEAK POSITION / SPACING d → PHASE IDENTIFICATION ANALYSIS/LATTICE CONSTANT

HALF WIDTH → CRYSTALLITE SIZE/LATTICE DEFORMATION

INTENSITY / RELATIVE INTENSITY OF PEAKS → PREFERRED ORIENTATION

ROCKING CURVE MEASUREMENT → DEGREE OF PREFERRED ORIENTATION

INTENSITY vs ANGLE (2θ)

[CANCEL] [<BACK] [NEXT>] [END]

4. SET AUTOMATIC ANALYSIS

TRANSPARENT CONDUCTIVE FILM (4/5) – SET AUTOMATIC ANALYSIS

PLEASE SELECT MEASUREMENT FOR AUTOMATIC ANALYSIS

☑ STUDY FILM THICKNESS/DENSITY/ROUGHNESS — SET CONDITIONS...

☑ STUDY CRYSTAL PHASE ($\theta/2\theta$ MEASUREMENT) — SET CONDITIONS...

☑ STUDY CRYSTALLITE SIZE/LATTICE DEFORMATION (STACKING DIRECTION) — SET CONDITIONS...    ← 46d

[CANCEL] [<BACK] [NEXT>] [END]

5. CONFIRM SELECTED CATEGORY

| TRANSPARENT CONDUCTIVE FILM (5/5) – CONFIRM SELECTED CATEGORY |
|---|

THE FOLLOWING MEASUREMENT WILL BE PERFORMED

EVALUATION MATERIAL: ZnO

STUDY FILM STRUCTURE: FILM THICKNESS VALUE:
UP TO 100 nm(AUTOMATIC ANALYSIS)

STUDY CRYSTAL PHASE:
θ/2θ MEASUREMENT (AUTOMATIC ANALYSIS)

STUDY CRYSTALLITE SIZE/LATTICE DEFORMATION:
STACKING DIRECTION(AUTOMATIC ANALYSIS)

[CANCEL]  [<BACK]  [NEXT>]  [END]

FIG. 15

5. CONFIRM SELECTED CATEGORY

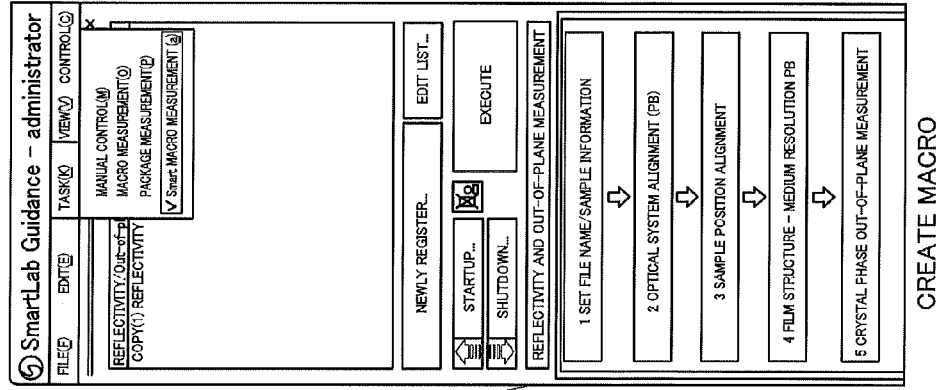

TRANSPARENT CONDUCTIVE FILM (5/5) – CONFIRM SELECTED CATEGORY

THE FOLLOWING MEASUREMENT WILL BE PERFORMED

EVALUATION MATERIAL: ZnO

STUDY FILM STRUCTURE: FILM THICKNESS VALUE:
UP TO 100 nm (AUTOMATIC ANALYSIS)

STUDY CRYSTAL PHASE:
$\theta/2\theta$ MEASUREMENT (AUTOMATIC ANALYSIS)

STUDY CRYSTALLITE SIZE/LATTICE DEFORMATION:
STACKING DIRECTION (AUTOMATIC ANALYSIS)

CANCEL  <BACK  NEXT>  END

55a

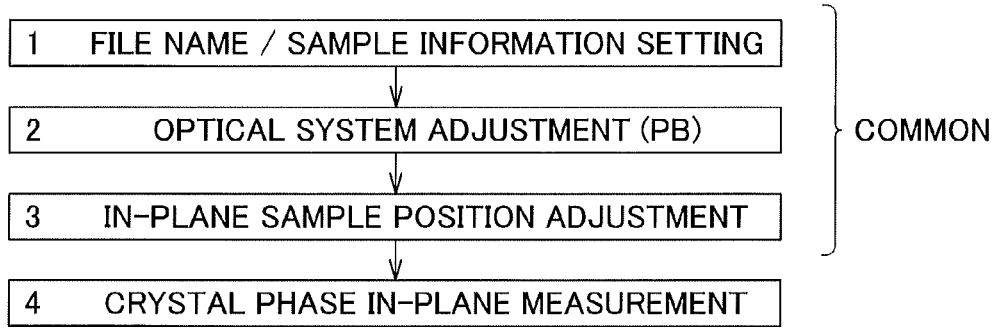
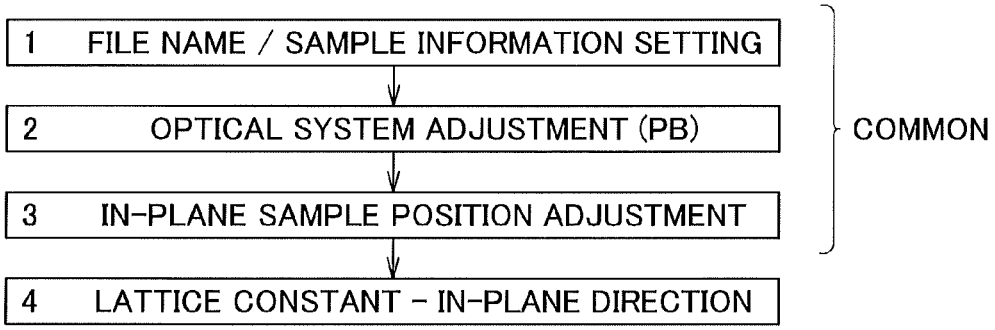
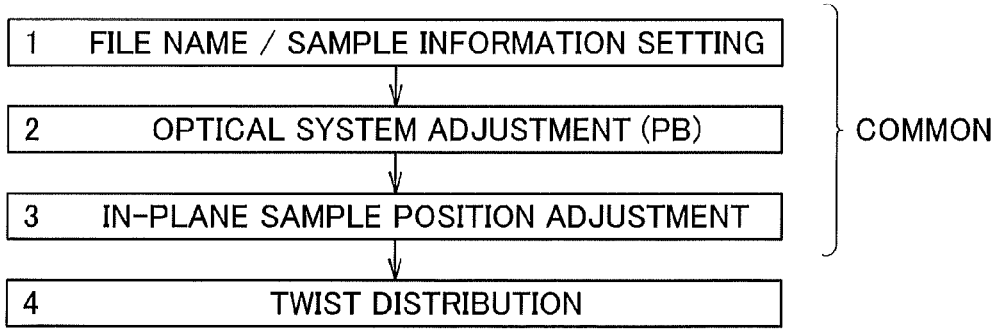

PHASE IDENTIFICATION
→ IN-PLANE MEASUREMENT

STUDYING FILM
THICKNESS/DENSITY/ROUGHNESS
→ FILM THICKNESS UP TO 100 nm

} COMMON

X-RAY ANALYSIS APPARATUS

BACKGROUND OF THE INVENTION

1. Field of the Invention

The present invention relates to an X-ray analysis apparatus having a function enabling a variety of measuring methods to be implemented.

2. Description of the Related Art

In recent years, there have been proposed X-ray analysis apparatuses having a function enabling a variety of measuring methods to be implemented. For example, according to Patent Citation 1, it is disclosed that X-ray diffraction measurement, X-ray small-angle scattering measurement, reflectivity measurement, and other measurement methods in which X-ray is used are performed using a single X-ray analysis apparatus.

According to, e.g., Patent Citation 2, there is disclosed an X-ray analysis apparatus in which the measurement method is predefined, the X-ray analysis apparatus making it possible to readily select, using a computer, a measurement condition that corresponds to the characteristics of the substance to be measured.

(Patent Citation 1): JP-A 2008-057989
(Patent Citation 2): JP-A 06-074923
(Problems to be solved by the invention)

In the X-ray analysis apparatus disclosed in Patent Citation 1, a configuration is present in which a variety of types of X-ray optical elements can be attached to and detached from a predetermined position in a single analysis apparatus as required. Therefore, selecting the desired X-ray optical element and disposing the X-ray optical element at the predetermined position make it possible to perform different types of X-ray measurement as required.

In industry, there are a variety of materials for which measurements and analyses using X-rays are desired. These materials belong to the field of semiconductor epitaxial films, semiconductor polycrystal films, magnetic films, or other material fields. A single material may belong to different material fields. There are a variety of such combinations of material fields and materials, and there is defined an appropriate evaluation method with respect to each combination of material fields and materials.

For example, it is known that characteristics of ZnO, ITO, and other materials belonging to a material field of electrode films used as transparent electrodes are preferably evaluated using measurement such as phase identification analysis measurement or preferred orientation analysis measurement. It is known that, e.g., when phase identification analysis measurement is performed, it is preferable that in-plane measurement is performed as the measurement method, and that an optical system including a parallel beam optical element and a receiving Soller slit is used as an optical system. It is also known that when preferred orientation analysis measurement is performed, it is preferable that rocking curve measurement is performed as the measurement method, and that, again, an optical system including a parallel beam optical element and a receiving slit is used as the optical system.

Thus, in an instance in which both the material to be measured and the material field to which the material belongs are specified, an appropriate category for evaluation, an appropriate measurement method, and an appropriate optical system are inevitably defined with respect to the combination of the material and the material field. However, deciding, with respect to a given combination of material and material field, the category for evaluation to be set, the measurement method to be employed, and the optical system to be employed is extremely difficult even for an experienced engineer, and is almost impossible for an operator lacking in knowledge of X-ray measurement.

As described above, according to the X-ray analysis apparatus in Patent Citation 1, it is possible to perform a variety of types of X-ray measurement such as in-plane measurement and rocking curve measurement as required. However, since it is extremely difficult to select a suitable measurement method and the like with respect to the material and other parameters, the available functionality cannot be fully utilized.

Also, according to the X-ray analysis apparatus of Patent Citation 2, it is readily possible, when the category for evaluation is already defined in advance, or specifically, when the category for evaluation is already defined in advance to be phase identification analysis, to decide, using a computer, the measurement condition suitable for the phase identification analysis. However, as with the instance of Patent Citation 1, it is up to the discretion of the measurement personnel to decide which category for evaluation, measurement method, and optical system to employ when the combination of the material and the material field has been decided. Therefore, measurement that is most suitable in relation to the material is often not performed, and correct data for evaluating the material is not obtained.

SUMMARY OF THE INVENTION

With the above problems in conventional apparatuses in view, a first object of the present invention is to enable, in an X-ray analysis apparatus having a function enabling a plurality of measurement methods (in-plane measurement, rocking curve measurement, and the like) to be implemented, the corresponding measurement functions of X-ray analysis apparatus to be utilized effectively.

An X-ray analysis apparatus according to a first aspect of the present invention for achieving the abovementioned first object is an X-ray analysis apparatus having a function for enabling a variety of measurement methods to be implemented, the X-ray analysis apparatus having: a measurement system capable of implementing a variety of measurement methods; measurement software for implementing, in a selective manner, each of the measurement methods; memory means for storing information relating to a material that may be measured (e.g., name of material, name of material field), and a name of an evaluation performed on the material; input means for inputting the information relating to the material; evaluation name computation means for performing computation for selecting the name of an evaluation on the basis of the information relating to the material inputted using the input means; and measurement method selection means for selecting a corresponding measurement method on the basis of the selected name of the evaluation.

The information relating to a material is, e.g., the name of the material, the name of the material field, the size of the material, and the like.

According to the above X-ray analysis apparatus according to the first aspect, merely inputting the information relating to the material makes it possible for anyone to establish, in a simple and accurate manner, the evaluation method (e.g., phase identification analysis, crystallinity evaluation, and the like) suited to the material and a measurement method suited to the material. Therefore, according to the present invention, it is possible to accurately select, from a variety of measurement functions available in the X-ray analysis apparatus, a measurement function that is most suitable for the material;

and it is therefore possible to effectively utilize the variety of functions available in the X-ray analysis apparatus.

In the X-ray analysis apparatus according to the first aspect, the information relating to the material may include a name of a material field. Examples of the name of the material field include semiconductor epitaxial film, barrier film, dielectric film, nanomaterial, and the like. Including the name of the material field as information relating to the material makes it possible to provide, through image display, the user with information regarding which evaluation (e.g., phase identification analysis, crystallinity evaluation, and the like) to perform in relation to which field the material belongs to. Therefore, the user can select, in a simple and reliable manner, which evaluation to perform.

In the X-ray analysis apparatus according to the first aspect, the information relating to the material may include a name of the material. The name of the material may be a chemical composition such as Si, Cu, or $FeSi_2$, or may be a designation of characteristics, such as low-molecular material or nanoparticles. Including the name of the material as information relating to the material makes it possible to provide, through image display, the user with information regarding which evaluation (e.g., phase identification analysis, crystallinity evaluation, and the like) to perform on which type of material. Therefore, the user can select, in a simple and reliable manner, which evaluation to perform.

In the X-ray analysis apparatus according to the first aspect, the information relating to the material may include both a name of a material field and a name of the material. It is thereby possible for the user to be provided with even more accurate information as to which is an appropriate evaluation to be performed on the material.

The X-ray analysis apparatus according to the first aspect may further have: memory means for storing the configuration of a variety of types of optical system; and optical system computation means for performing computation in which an appropriate optical system configuration is selected from the variety of types of optical system on the basis of a combination of the name of the evaluation and the measurement method.

This configuration makes it possible to appropriately select the optical system for implementing a measurement method without being influenced by the subjective view of the user.

The X-ray analysis apparatus according to the first aspect may have input means for inputting the size of the material. The optical system computation means may use the inputted size of the material as a determining material for the computation for selecting the configuration of the optical system.

According to this configuration, the size of the material is added as a determining parameter when selecting the optical system. Therefore, the optical system can be selected in an even more appropriate manner with regard to the material.

As described above, according to the X-ray analysis apparatus according to the first aspect of the present invention, a variety of measurement methods such as out-of-plane measurement, in-plane measurement, and rocking curve measurement can be implemented using a computer in order to implement a variety of evaluations such as phase identification analysis evaluation, crystallinity evaluation, and film thickness evaluation. In this instance, it is possible to accumulate, in advance, the correspondence relationship between a variety of material names and a variety of evaluation names as a database, and in an instance in which a user inputs a material name, use the database to notify the user of which evaluation is suitable for the material. It is thus possible to operate an X-ray analysis apparatus equipped with a variety of measurement methods in an effective and functional manner.

Generally, when a single measurement method such as in-plane measurement is to be implemented using a computer, the computer may be used to create a macro for the measurement method, and the macro may be written as necessary into a program, whereby the measurement method is implemented. As is well known, a macro is a simple program in which a process comprising a plurality of command steps is defined in advance as a single command.

This macro is generally formed by consecutively combining a plurality of process steps. For example, as shown in FIG. 17A, in an instance in which crystallinity evaluation is performed using a measurement method of in-plane measurement, a macro is configured by consecutively combining step 1 for setting the file name and sample information, step 2 for performing an optical system adjustment on a specific optical component, step 3 for performing in-plane sample position adjustment, and step 4 for measuring the phase identification using in-plane measurement.

Also, as shown in FIG. 17B, in an instance in which an evaluation, in which the lattice constant within surface plane direction is to be studied, is to be performed using a measurement method of in-plane measurement, a macro is configured by consecutively combining step 1 for setting the file name and sample information, step 2 for performing an optical system adjustment on a specific optical component, step 3 for performing in-plane sample position adjustment, and step 4 for measuring the lattice constant within surface plane direction using in-plane measurement.

In recent years, there are situations, as with the X-ray analysis apparatus of Patent Citation 1, in which the use of a plurality of measurement axes or the use of a plurality of optical components is controlled in a single apparatus, whereby a plurality of different measurement methods are successively executed in a single apparatus. For example, there is an instance in which the measurement method shown in FIG. 17A and the measurement method shown in FIG. 17B are successively executed. In such an instance, according to a conventional macro creation method, the final macro is normally configured by consecutively linking the macros shown in FIGS. 17A and 17B. However, when a method of such description is employed, a problem may occur in which the user is required to repeatedly perform similar actions or in which the control flow itself becomes cumbersome.

A second object of the X-ray analysis apparatus according to another aspect of the present invention is to resolve this conventional problem related to macros, i.e., to make it possible, in an X-ray analysis apparatus having a function enabling a plurality of measurement methods (in-plane measurement, rocking curve measurement, and the like) to be implemented, to effectively utilize the measurement functions without greatly burdening the user or greatly burdening the control flow.

An X-ray analysis apparatus according to the second aspect of the present invention for achieving the abovementioned second object is an X-ray analysis apparatus having a function for enabling a plurality of measurement methods to be implemented, the X-ray analysis apparatus having: a measurement system capable of implementing a plurality of measurement methods; measurement software for implementing, in a selective manner, each of the measurement methods; and macro creation means for creating a macro for implementing the measurement methods; wherein the macro creation means is capable of creating a macro, comprising a plurality of part steps, for implementing each of the plurality of measurement methods; and in an instance in which at least two of the plurality of measurement methods are being implemented, and macros corresponding to each of the measurement methods include identical part steps, the macro creation means creates a macro in which execution of at least one of the identical part steps is omitted and part steps that differ between each of the measurement methods are sequentially executed.

The X-ray analysis apparatus according to a second aspect is an X-ray analysis apparatus having a function enabling a plurality of measurement methods (in-plane measurement, rocking curve measurement, and the like) to be implemented. According to this X-ray analysis apparatus, when a plurality of measurement methods are successively executed, at least one of part steps that are identical between macros corresponding to each of the measurement methods is omitted, instead of every one of the part steps constituting macros corresponding to individual measurement methods being executed. Therefore, it is possible, when a plurality of measurement methods are executed using the X-ray analysis apparatus of the present invention, to implement the plurality of measurement methods without greatly burdening the user in terms of workload and without greatly burdening the control flow in the macro.

Next, an X-ray analysis apparatus according to a third aspect of the present invention for achieving the abovementioned second object is an X-ray analysis apparatus having a function for enabling a plurality of measurement methods to be implemented, the X-ray analysis apparatus having: a measurement system capable of implementing a plurality of measurement methods; measurement software for implementing, in a selective manner, each of the measurement methods; and macro creation means for creating a macro for implementing the measurement methods; wherein the macro creation means is capable of creating a macro, comprising a plurality of part steps, for implementing each of the plurality of measurement methods; and in an instance in which at least two of the plurality of measurement methods are being implemented, and a function of a part step included in a first macro, which is one of the macros corresponding to each of the measurement methods, encompasses a function of a part step included in a second macro, which is another macro, the macro creation means creates a macro in which the part step belonging to the first macro is used while the part step belonging to the second macro is not used, and part steps that differ between each of the measurement methods are sequentially executed.

In the above configuration, an instance in which "a function of a part step (meaning a step forming a part (namely, one component) of a macro) included in a first macro, which is one of the macros corresponding to each of the measurement methods, encompass a function of a part step included in a second macro, which is another macro" refers to an instance in which, e.g., the first macro includes a step for performing an in-plane sample position adjustment, and a second macro includes a step for a regular sample position adjustment employed in a normal goniometer.

In a step for a regular sample position adjustment, the accuracy in adjusting the sample position need not be particularly high, whereas in a step for an in-plane sample position adjustment, it is necessary to adjust the sample position to a high degree of adjustment accuracy. In other words, in terms of functionality, performing an in-plane sample position adjustment achieves the function of a regular sample position adjustment, whereas performing a regular sample position adjustment does not achieve the function of an in-plane sample position adjustment.

In other words, the in-plane sample position adjustment step included as a part step in the first macro has a function that encompasses the function of the normal sample position adjustment included as a part step in the second macro.

The X-ray analysis apparatus according to the third aspect is an X-ray analysis apparatus having a function enabling a plurality of measurement methods (in-plane measurement, rocking curve measurement, and the like) to be implemented. According to this X-ray analysis apparatus, when a plurality of measurement methods are successively executed, in an instance in which a function of a part step included in the first macro, which is one of the macros corresponding to each of the measurement methods, encompasses a function of a part step included in a second macro, which is another macro, the part step belonging to the first macro is used while the part step belonging to the second macro is not used, instead of every one of the part steps constituting macros corresponding to individual measurement methods being executed. Therefore, it is possible, when a plurality of measurement methods are executed using the X-ray analysis apparatus of the present invention, to implement the plurality of measurement methods without greatly burdening the user in terms of workload and greatly burdening the control flow in the macro.

BRIEF DESCRIPTION OF THE DRAWINGS

FIG. 7 illustrates an example of image display;

FIG. 8 illustrates another example of image display;

FIG. 10 illustrates a still another example of image display;

FIG. 11 illustrates a still another example of image display;

FIG. 12 (consisting of FIGS. 12A and 12B) illustrates a still another example of image display;

FIG. 13 illustrates a still another example of image display;

FIG. 14 illustrates a still another example of image display;

FIG. 15 illustrates a still another example of image display;

FIG. 16 is a flow chart illustrating an example of flow of computation for selecting the measurement method and the like;

FIGS. 17A, 17B and 17C illustrate examples of a macro;

DESCRIPTION OF THE PREFERRED EMBODIMENTS

Figure 1:
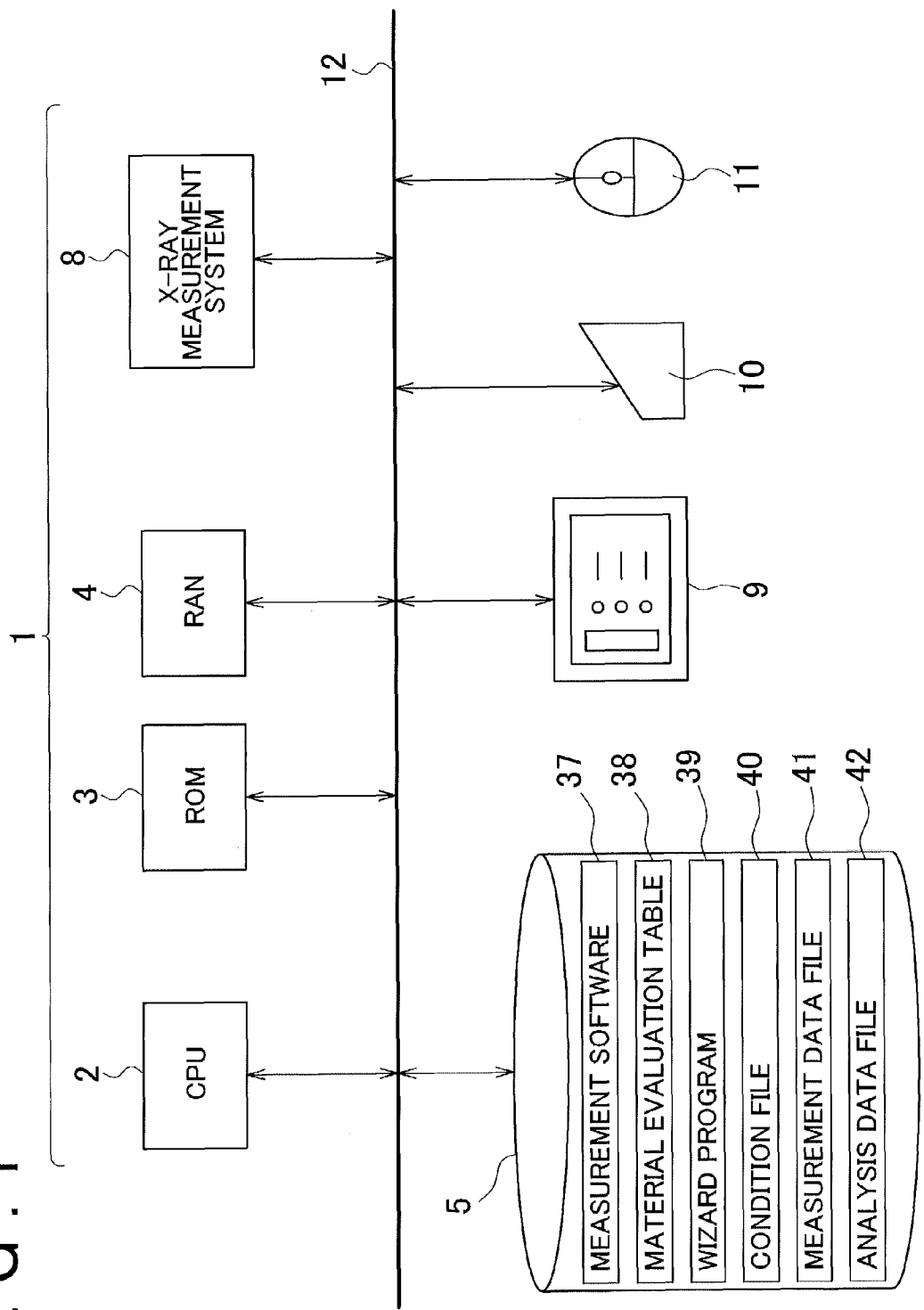
FIG. 1 is a block diagram showing an embodiment of an X-ray analysis apparatus according to the present invention.

The X-ray analysis apparatus according to the present invention will now be described on the basis of an embodiment. It shall be apparent that the embodiment is not provided by way of limitation to the present invention. In the drawings accompanying the present specifications, constituent elements may be shown at a proportion different to that in reality, so that characteristic portions are shown in a manner that is easily understood.

FIG. 1 shows an embodiment of the X-ray analysis apparatus according to the present invention. The X-ray analysis apparatus according to the present embodiment, the entirety of which is represented by numeral 1, has: a CPU 2, which is a central processing control device of the computer; a read-only memory (ROM) 3; a random-access memory (RAM) 4; and a memory unit 5, which is a storage medium. The ROM 3 and the RAM 4 form an internal memory of a computer.

The memory unit 5 comprises semiconductor memory, a hard disk, or another storage medium of choice. The memory unit 5 may be installed internally with respect to the computer, or may be installed externally with respect to the computer. The memory unit 5 may be a single unit, or may be a plurality of storage media. The CPU 2 implements predetermined functions according to programs stored in the memory unit 5 while accessing the ROM 3 and the RAM 4 as required.

The X-ray analysis apparatus 1 also has: an X-ray measurement system 8, which is a measurement mechanism for using X-ray and implementing a plurality of types of measurement methods; a display 9 corresponding to image display means for displaying an image; a keyboard 10 corresponding to input means; and a mouse 11, which also corresponds to input means. The above elements are connected to each other by a data bus 12.

Figure 2:
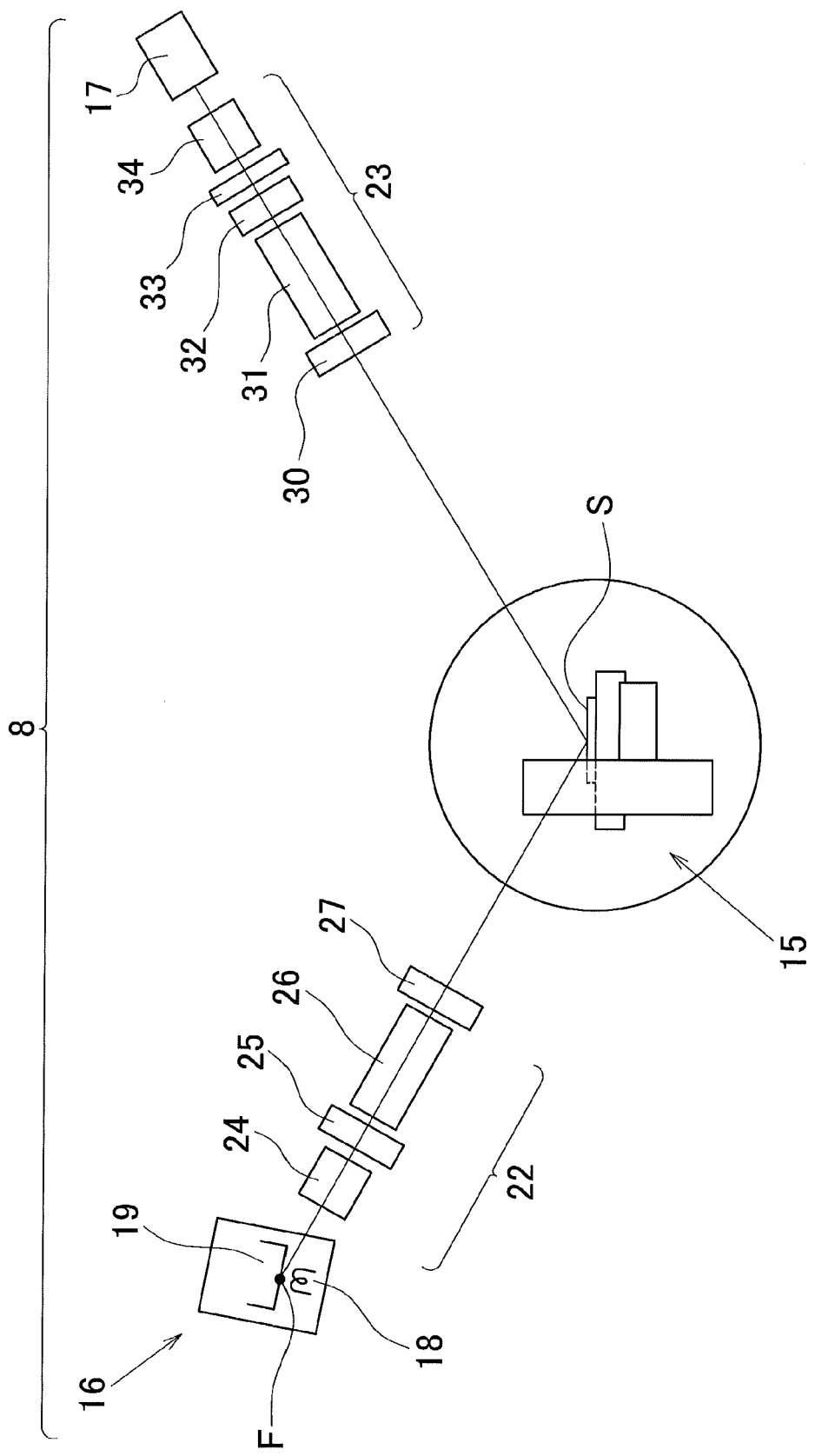
FIG. 2 illustrates the configuration of an X-ray measurement system, which is a principal part of the X-ray analysis apparatus shown in FIG. 1.

As shown in FIG. 2, in the present embodiment, the X-ray measurement system 8 has: a goniometer 15, which is an angle-measuring instrument; an X-ray generation device 16 installed on one side of the goniometer 15; and an X-ray detector 17 installed on the other side of the goniometer 15. A filament 18, which is a cathode; and a target 19, which is an anti-cathode, are provided to the interior of the X-ray generation device 16. A region at which electrons released from the filament 18 strike the surface of the target 19 is an X-ray focus F, and X-ray is generated from the X-ray focus F. In other words, the X-ray focus F functions as an X-ray source.

In the present embodiment, a 2 kW sealed tube in which a copper (Cu) target is used as the X-ray generation device 16. The X-ray focus F measures 1 mm×10 mm. An exiting X-ray beam may have a point-focus or a line-focus cross-sectional profile depending on the requirement.

The X-ray detector 17 may be a zero-dimensional X-ray detector having no positional resolution ability; a one-dimensional X-ray detector having a positional resolution ability in a linear direction; or a two-dimensional X-ray detector having a positional resolution ability within a two-dimensional field. Examples of a zero-dimensional X-ray detector include a proportional counter or a scintillation counter. Examples of a one-dimensional X-ray detector include a position-sensitive proportional counter (PSPC) or a linear charge-coupled device (CCD). Examples of a two-dimensional X-ray detector include a two-dimensional CCD sensor, or photon-counting-type pixel two-dimensional detector. A photon-counting-type pixel two-dimensional detector is an X-ray detector comprising a plurality of pixels, which directly convert photons excited by X-ray into an electric signal and output the electric signal, arranged two-dimensionally. A photon-counting-type pixel two-dimensional detector is capable of detecting X-ray by each pixel and outputting a signal by each pixel.

An incident optical system 22 is provided between the X-ray generation device 16 and the goniometer 15. A receiving optical system 23 is provided between the goniometer 15 and the X-ray detector 17. The incident optical system 22 has a cross-beam optics (CBO) unit 24, a monochromator unit 25, an incident optical unit 26, and an incident slit box 27.

Slits, such as a focusing slit (BB), a parallel-beam slit (PB), a small-angle scattering measurement slit (SA), and a microarea measurement slit (MA), can be attached to or detached from the CBO unit 24. It is also possible to simply have a space with no slit being present.

A monochromator can be attached to or detached from the monochromator unit 25. It is possible to simply have a space with no monochromator being present. For the monochromator, a 2-crystal monochromator Ge (220)×2, a 2-crystal monochromator Ge (400)×2, a 4-crystal monochromator Ge (220)×4, and a 4-crystal monochromator Ge (440)×4 are selectively used.

A necessary slit can be attached to, and detached from, the incident optical unit 26. It is also possible to have a simple space with no slit being present. A plurality of types of Soller slits or in-plane parallel slit collimators (PSC) are selectively used as a slit.

A slit can be attached to, and detached from, the incident slit box 27. It is also possible to have a simple space with no slit being present. Examples of the slits include a plurality of types, e.g., 5 types, of length-limiting slits within a range of, e.g., 0.5 mm to 15 mm.

The receiving optical system 23 has a first receiving slit box 30, a first receiving optical unit 31, a second receiving optical unit 32, a second receiving slit box 33, and an attenuator unit 34. An appropriate filter (CuKβ filter in the present embodiment) can be attached to, and detached from, the first receiving slit box 30. It is possible to have a simple space with no filter being present.

An appropriate analyzer device can be attached to, and detached from, the first receiving optical unit 31. It is also possible to have a simple space with no analyzer being present. A 2-crystal analyzer Ge (220)×2 and a 2-crystal analyzer Ge (400)×2 are selectively used as the analyzer. A plurality of types of parallel slit analyzers (PSAs) between which angles are different are also selectively used as the analyzer. As for the angle of the PSA, e.g., 1.0°, 0.5°, 0.114°, and 0.05° are used.

A Soller slit and an in-plane parallel slit analyzer (PSA) can be selectively attached to, and detached from, the second receiving slit box 32. It is also possible to have a simple space with no slit or similar element being present. For the Soller slit, e.g., Soller slit 5.0 deg and Soller slit 2.5 deg are used. For the in-plane PSA, e.g., In-plane PSA 1.0 deg, In-plane PSA 0.5 deg, and In-plane PSA 0.114 deg are used.

A slit can be attached to, and detached from, the second receiving slit box 33. It is also possible to have a simple space with no slit being present.

An attenuator can be attached to, and detached from, the attenuator unit 34. It is also possible to have a simple space with no attenuator being present. For the attenuator, e.g., several types of aluminum (Al) plates having different thicknesses for attenuating X-ray are selectively used. For the Al plate having different attenuation coefficients, e.g., $\frac{1}{10,000}$, $\frac{1}{1,000}$, and $\frac{1}{70}$ are used.

Figure 3:
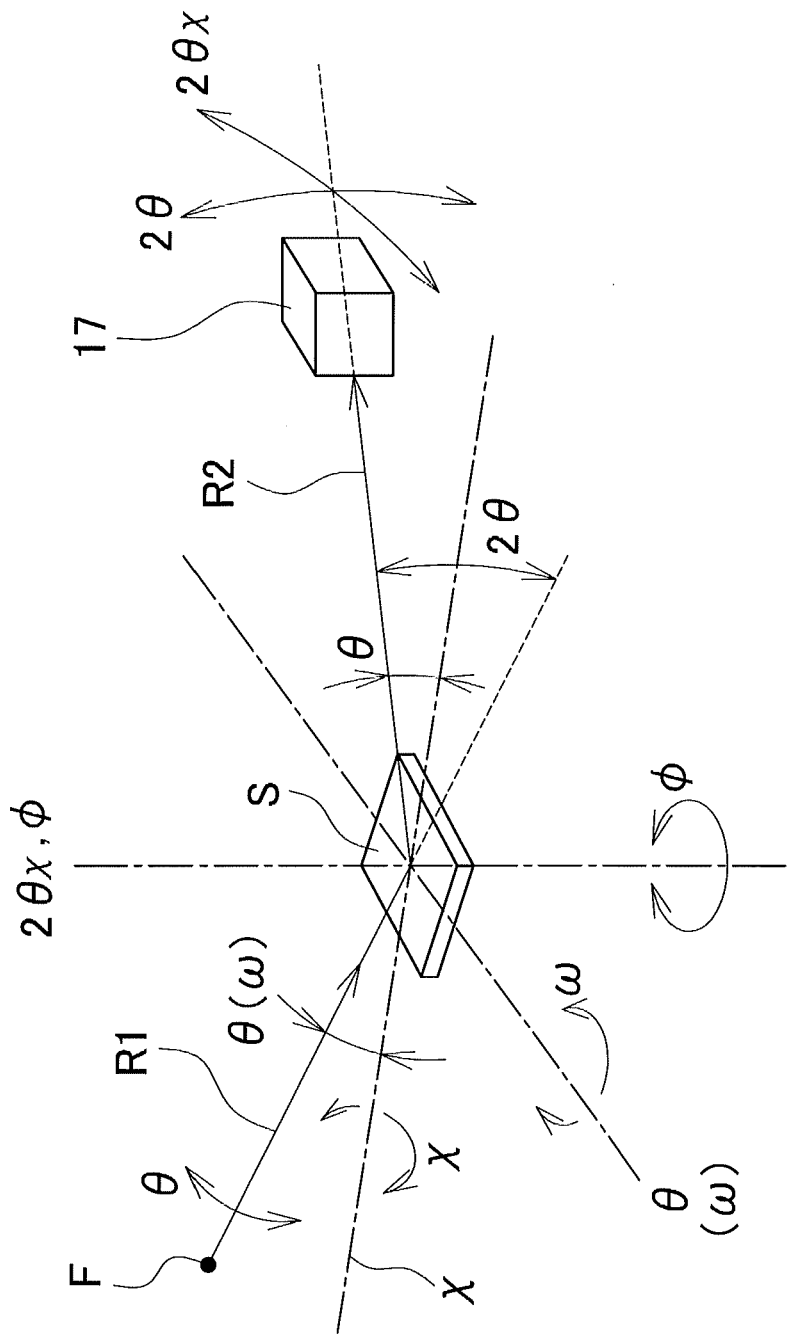
FIG. 3 illustrates the function of a goniometer, which is a principal part of the X-ray analysis apparatus shown in FIG. 2.

The goniometer 15 is capable of implementing a plurality of measurement methods shown in FIG. 3. In FIG. 3, a sample S is placed at a predetermined position by a sample support device or a sample support plate (not shown). The sample support device or the sample support plate is a constituent element of the goniometer 15. In the present embodiment, the sample S is placed within a horizontal plane. The sample S may also be placed within a perpendicular plane.

In the present embodiment, the term "axial line," as in "θ-axial line," refers to the line itself, such as an imaginary line; and the term "axis," as in "θ-axis," refers to a support system for supporting a variety of components so as to be capable of rotation around the above-mentioned "axial line" or so as to be capable of movement along the "axial line."

1. Out-of-Plane Measurement

In FIG. 3, an X-ray source F is provided on one side of the position at which the sample S is placed. The X-ray source F is an X-ray focus formed on a surface of an anode (target) disposed opposite, e.g., a filament or another cathode. Specifically, a region at which electrons generated from the cathode strike the surface of the anode is an X-ray focus, and X-rays are released from the X-ray focus. In the present embodiment, the X-ray focus is the X-ray source F.

Although X-rays are emitted from the X-ray focus F in all directions in three dimensions, X-rays released in a specific angular region exit to be emitted as an incident X-ray R1 onto the sample S. When crystal lattice planes in the sample S satisfy the Bragg's diffraction condition with respect to the incident X-ray R1, a diffracted X-ray R2 is generated from the sample S. In the present embodiment, the diffracted X-ray R2 is detected by the X-ray detector 17.

In the present embodiment, a θ-axial line is set so as to pass through the surface of the sample S placed at a predetermined measurement position and so as to be parallel to the surface of the sample. The θ-axial line is set so as to be fixed. Rotationally moving the sample S relative to the X-ray source F about the θ-axial line makes it possible to vary the incidence angle θ of the incident X-ray R1 with respect to the sample S. Rotationally moving the X-ray source F relative to the sample S about the θ-axial line also makes it possible to vary the incidence angle θ. A rotational movement of such description of the X-ray source F or the sample S about the θ-axial line shall be referred to as a θ-rotation of the sample S.

Supposing that the diffracted X-ray R2 is generated when the X-ray is incident on the sample S at an incidence angle θ, the angle 2θ of the diffracted X-ray R2 with respect to the incident X-ray R1 (this angle 2θ shall hereafter be referred to as the "diffraction angle") will be twice the size of θ. The X-ray detector 17 rotationally moves about the θ-axial line so as to maintain an angle twice the size of the X-ray incident angle θ, so that the diffracted X-ray R2 generated at diffraction angle 2θ can be detected. A rotational movement of such description of the X-ray detector 17 about the θ-axial line shall be referred to as a 2θ-rotation of the X-ray detector 17.

Thus causing the X-ray source F or the sample S to perform a θ-rotation about the θ-axial line, and causing the X-ray detector 17 to perform a 2θ-rotation about the θ-axial line in synchronization therewith, is referred to as a "θ/2θ-scan." The expression "A/B" (where each of A and B represents an operating axis) indicates that the motion of A and the motion of B are coupled, i.e., interlinked.

A plane including the center line of the incident X-ray R1 incident on the sample S and the center line of the diffracted X-ray R2 from the sample S is generally called an equatorial plane, or out-of-plane. An out-of-plane measurement can be performed by causing the X-ray source F and the X-ray detector 17 to perform a θ/2θ-scan as described above and performing a measurement.

2. In-Plane Measurement

In FIG. 3, there is set a $2\theta_X$ (theta-chi) axial line, which perpendicularly penetrates the sample S placed at the predetermined sample position and which is at a right angle with respect to the fixed θ-axial line. If the θ-axial line is a horizontal line, the $2\theta_X$-axial line is a perpendicular axial line; and if the θ-axial line is a perpendicular axial line, the $2\theta_X$-axial line is a horizontal axial line. There is also set a φ-axial line, which is an axial line that orthogonally intersects the surface of the sample S placed at the predetermined sample position. In FIG. 3, the φ-axial line and the $2\theta_X$-axial line overlap and form a single line. However, while the $2\theta_X$-axial line is a fixed line, the φ-axial line is an axial line that moves in correspondence with the movement of the sample S when the sample S moves in a swinging or a slanted motion.

A direction that is at a right angle with respect to the equatorial plane, which includes the center line of the incident X-ray R1 incident on the sample S and the center line of the diffracted X-ray R2 from the sample S, is generally called a latitude direction or an "in-plane" direction. In the present embodiment, there is provided a driving system for rotationally moving the X-ray detector 17 around the $2\theta_X$-axial line. Rotationally moving the X-ray detector 17 around the $2\theta_X$-axial line by the driving system makes it possible to move the X-ray detector 17 in the in-plane direction. A movement of the X-ray detector 17 in the in-plane direction of such description is called a $2\theta_X$-scan.

In the present embodiment, there is also provided a driving system for rotationally moving the sample S around the φ-axial line, which orthogonally intersects the sample S itself. Rotationally moving the sample S around the φ-axial line is generally called a φ-scan. The rotation of the sample S within a two-dimensional field, caused by the φ-scan, is generally called a rotation of sample S within surface plane thereof.

Causing the sample S to perform a φ-scan and causing the X-ray detector 17 to perform a $2\theta_X$-scan make it possible to obtain useful X-ray diffraction data relating to the sample S. A measurement method of such description is generally called in-plane measurement.

3. Rocking Curve Measurement (ω-Scan)

A rocking curve is a diffraction intensity curve measured when an X-ray beam having high monochromaticity and parallelism is made incident on a sample crystal, and the angle of incidence of the X-ray with respect to the sample is slowly rotated at a constant low speed in the vicinity of an angle satisfying the Bragg's diffraction condition. Normally, this curve is drawn on a graph in which the horizontal axis represents the angle of X-ray incidence and the vertical axis represents the X-ray intensity.

In FIG. 3, the angle θ of the incident X-ray R1 incident from the X-ray source F onto the sample S (i.e., the X-ray incident angle θ) is sometimes conventionally called "angle ω" depending on the type of measurement. In the present embodiment, conventional naming will be respected, and depending on the type of measurement, the θ-axial line is referred to as an ω-axial line, the θ-axis is referred to as an ω-axis, and the θ-scan is referred to as an ω-scan.

Securing the position of the X-ray source F and the X-ray detector 17 and performing an ω-scan with the sample S or the X-ray source F make it possible to obtain a flat or a peak-shaped X-ray diffraction intensity diagram, i.e., a rocking curve. A measurement method thus performed is called rocking curve measurement by ω-scanning.

4. Rocking Curve Measurement (φ-Scan)

Securing the positions of the X-ray source F and the X-ray detector 17 and performing a φ-scan with the sample S around the φ-axial line as described above make it possible to obtain a flat or a peak-shaped diffraction line intensity diagram, i.e., a rocking curve. The measurement method thus performed is called rocking curve measurement by φ-scanning.

5. High-Resolution Rocking Curve Measurement (ω/2θ-Scan)

High-resolution rocking curve measurement is a measurement implemented by setting an incident 2-crystal or a 4-crystal monochromator and a receiving 2-crystal analyzer as constituent elements of an optical system, using an epitaxial thin film as the sample S, and performing a ω/2θ-scan.

6. High-Resolution In-Plane Measurement

There shall now be introduced for consideration a X-axial line, which is an axial line that passes the surface of the sample S placed at the predetermined sample position, and that orthogonally intersects both the θ-axial line and the $2\theta_X$-axial line. The angle of the sample S around the X-axial line may be referred to as a fanning or tilting angle X. As mentioned earlier, causing the sample S to perform a φ-scan and causing the X-ray detector 17 to perform a $2\theta_X$-scan make it possible to perform an in-plane measurement. However, instead of causing the sample S to perform a φ-scan and causing the X-ray detector 17 to perform a $2\theta_X$-scan, fixing the fanning or tilting angle X to 90° and causing the sample S to perform a ω/2θ-scan make it possible to perform a high-resolution in-plane measurement. A ω/2θ-scan refers to simultaneously performing a 2θ-scan in relation to the X-ray detector 17 and a ω-scan in relation to the sample S. Using this scan method makes it possible to perform a high-resolution in-plane measurement.

7. Grazing-Incident Measurement

With regard to FIG. 3, fixing the X-ray incident angle ω with respect to the sample S at a small angle of no greater than 1°, and causing the X-ray detector 17 to perform a 2θ-scan about the θ-axial line (i.e., the ω-axial line) to measure the diffracted X-ray, make it possible to measure the diffracted X-ray generated by a thin film formed on a substrate. The measurement method performed as described above is called Grazing-Incident measurement.

8. Pole Figure Measurement

Figure 4:
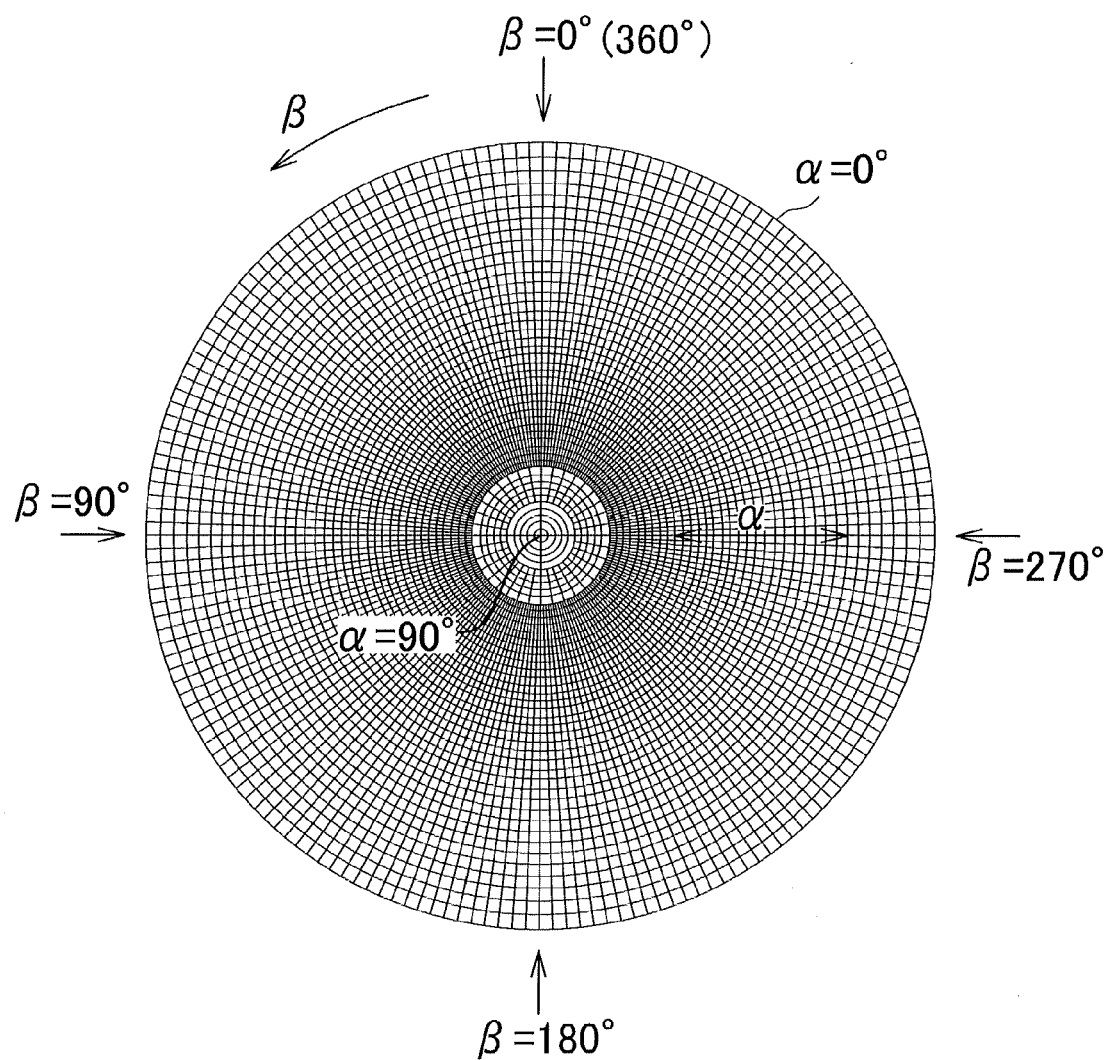
FIG. 4 illustrates an example of a polar net used in pole figure measurement, which is a measurement method.

Generally, an intersection between a sphere having the sample as the center (i.e., a projection sphere) and a normal of a lattice plane of the sample is known as a pole. A diagram obtained on a polar net shown in FIG. 4, which represents plane coordinates, by performing a stereo projection, i.e., a stereographic projection, of the projection sphere on the polar net is a pole figure. The pole figure is sometimes called a pole diagram. Using this pole diagram makes it possible to display, in an appropriate manner, texture of sample, i.e., the orientation, of a polycrystal, i.e., the preferred orientation in a polycrystal sample. The polar net shown in FIG. 4 represents polar coordinates in which the radial direction represents the angle α (°) and the circumferential direction represents the angle β (°).

The above-mentioned pole diagram can be measured, e.g., as follows. Specifically, with regard to FIG. 3, the X-ray incident angle θ is fixed, and the angle 2θ at which the X-ray detector 17 is disposed relative to the sample S is fixed. Then, while the angle (i.e., fanning or tilting angle) X of the sample S around a X-axial line, which is an axial line passing through the surface of the sample S placed on a predetermined sample position and orthogonally intersecting both the θ-axial line and the $2\theta_X$-axial line, and the angle φ of rotation within surface plane of the sample S around the φ-axial line, are caused to vary, a measurement is made for the intensity I of the diffracted X-ray at individual sample positions specified by the fanning or tilting angle X and the angle φ of rotation within surface plane. Pole figure data specified by (X, φ, I) is thereby measured.

Next, a predetermined conversion equation is used to convert a X-value to an α-value, a predetermined conversion equation is used to convert a φ-value to a β-value, and Pole figure data specified by (α, β, I) is obtained. The resulting (α, β, I) polar data is plotted on the polar net shown in FIG. 4, whereby a pole figure can be obtained. The pole figure measurement thus performed is known as a X-pole figure measurement.

Pole figure measurements are not limited to the X-pole figure measurement described above. For example, in JP-A 2001-056304, there is disclosed performing a correction on data obtained by X-ray analysis apparatus with $2\theta_X$-axis, to obtain a pole figure. A pole figure measurement thus performed is called an in-plane pole figure measurement.

9. Reciprocal Space Map Measurement (ω-steps, ω/2θ-scan)

A reciprocal space map is a diagram showing the intensity distribution of diffracted X-ray from a sample in a reciprocal space. A reciprocal space is, as is well known, a space formed by reciprocal lattice vectors; and is one in which the periodicity of real space is reflected. A reciprocal lattice vector is, as is well known, a vector defined by a predetermined relationship with a fundamental vector of a crystal in real space. In general, a reciprocal lattice point exists at the tip of a reciprocal lattice vector, and a plurality of reciprocal lattice points are arranged in the reciprocal space.

By creating and observing this reciprocal space map, it is possible to find out, e.g., fluctuations in the lattice constant of the crystal, the tilt of the lattice plane, and other parameters. According to the present embodiment, a measurement method is used in which the sample S is caused to undergo an incremental ω-movement, and a ω/2θ-scan is performed at each ω-position, whereby a reciprocal space map measurement can be performed.

10. Reciprocal Space Map Measurement (φ Steps, ω/2θ-Scan)

With regard to FIG. 3, using a measurement method in which the sample S is caused to undergo an incremental φ-movement (i.e., movement within surface plane) and a $\phi/2\theta_X$-scan is performed at each φ-position, makes it possible to perform a reciprocal space map measurement.

11. Wide-Region Reciprocal Space Map Measurement

With regard to FIG. 3, using a measurement method in which the sample S is caused to undergo an incremental X-movement and a $\phi/2\theta_X$-scan is performed at each X-position, makes it possible to perform a wide-region reciprocal space map measurement, i.e., a reciprocal space map measurement in which measurement can take place across a wide range within the reciprocal space.

12. Reflectivity Measurement

The refractive index of a substance in relation to X-ray is slightly smaller than 1; and if X-ray is incident on a substance at an extremely shallow angle, total external reflection will occur. The X-ray reflectivity can be obtained by measuring the X-ray reflection intensity in the vicinity of total reflection. The depth of X-ray entry into a substance in the vicinity of total reflection is extremely small, at about 10 to 100 nm from the surface, and X-ray reflectivity measurement is effective for evaluation in the vicinity of the surface of a substance or evaluation of a thin film or the like.

When performing a reflectivity measurement, the range of the angle ω of incidence of X-ray on the sample S is set to an extremely small angle of, e.g., about ω=0.1° to 4°, X-ray is caused to be totally reflected by the sample S, and the reflected X-ray is detected using the X-ray detector. In this reflectivity measurement device, subjecting the sample S to X-rays that have been precisely monochromatized; selecting, from the X-rays emerging from the sample S, only those X-rays that satisfy a predetermined angular resolution; and supplying only the selected X-rays to the X-ray detector, make it possible to obtain reflectivity data having a high degree of reliability.

In the present embodiment, a ω/2θ-scan is performed, i.e., a 2θ-scan and an ω-scan are executed in an interlinked manner, whereby the reflectivity is measured.

13. Transmission Small-Angle Scattering Measurement

In some substances, when X-rays are exposed to the substance, X-ray scattering may be generated at a small-angle region, e.g., an angular region of about 0° to 5°, around the optical axis of the incident X-ray. For example, if fine particles of about 10 to 1000 Å or regions having a corresponding size in which the density fluctuation exists are present in the substance, so-called diffuse scattering occurs in the direction of the incident ray. In this diffuse scattering, the spread of the scattering increases with decreasing particle size, irrespective of the internal structure of the particles. In the present embodiment, causing the X-ray detector 17 to perform a 2θ-scan makes it possible to perform small-angle scattering measurement, and particularly to measure scattered rays generated in a direction at which the rays are transmitted through the sample.

(Arithmetic Control System)

In FIG. 1, a variety of program software, files, and other data are stored in regions, each having the respectively necessary capacity, in the memory unit 5. In the drawing, for purposes of convenience, the items of software, files, and similar data are shown in a single memory unit. However, in reality, these items of program software may be divided and stored in a plurality of storage media according to necessity.

Specifically, measurement software 37, a material evaluation table 38, a wizard program 39 functioning as measurement assistance software, a condition file 40, a measurement data file 41, and an analysis data file 42 are set in the memory unit 5.

The measurement software 37 is program software for implementing, using the CPU 2, a predetermined function; and specifically, program software for individually performing a variety of measurement methods such as the above-mentioned out-of-plane measurement, in-plane measurement, and rocking curve measurement.

Figure 5A:
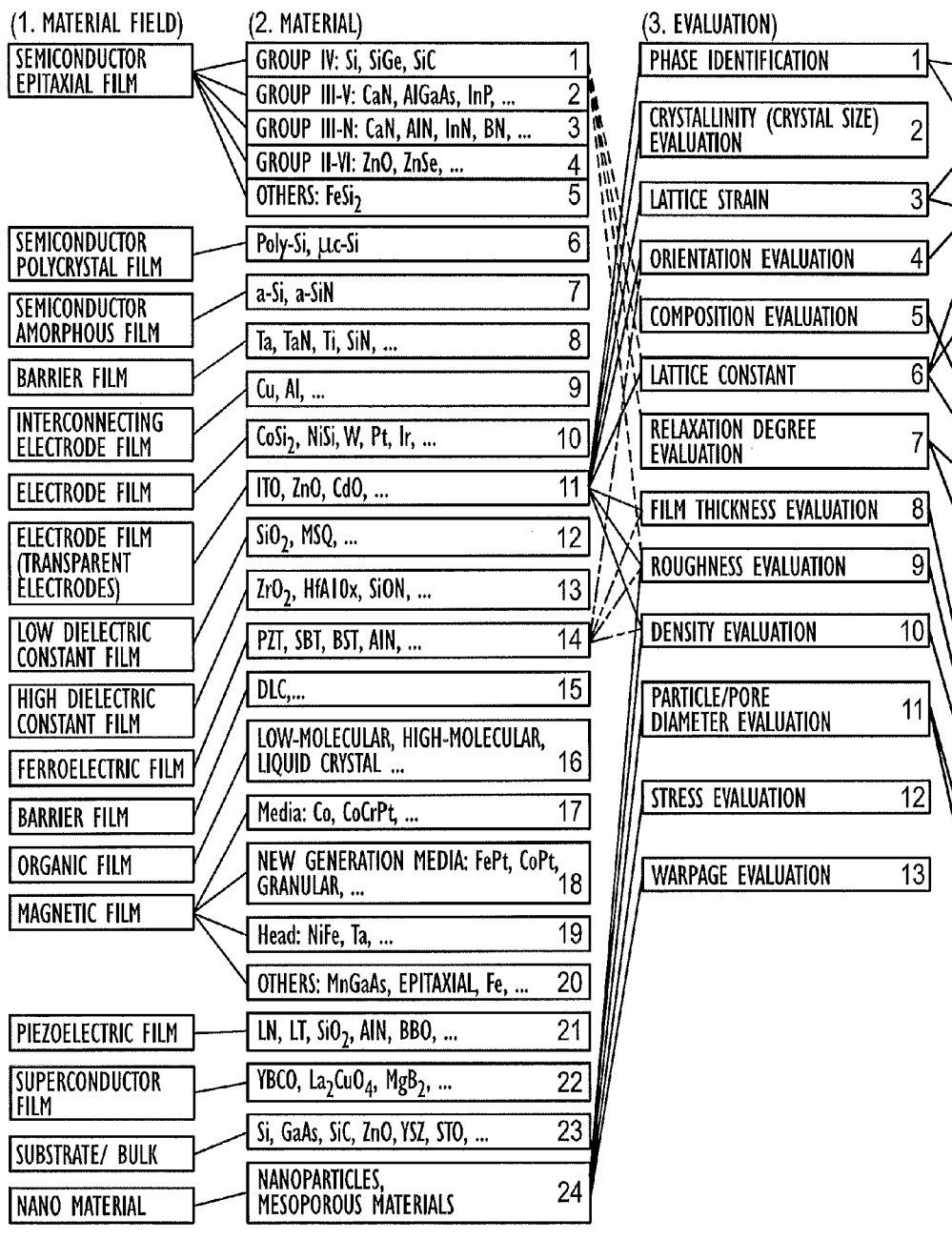
FIG. 5 (consisting of FIGS. 5A and 5B) is a schematic drawing showing details of data stored in the memory unit shown in FIG. 1.
Figure 5B:
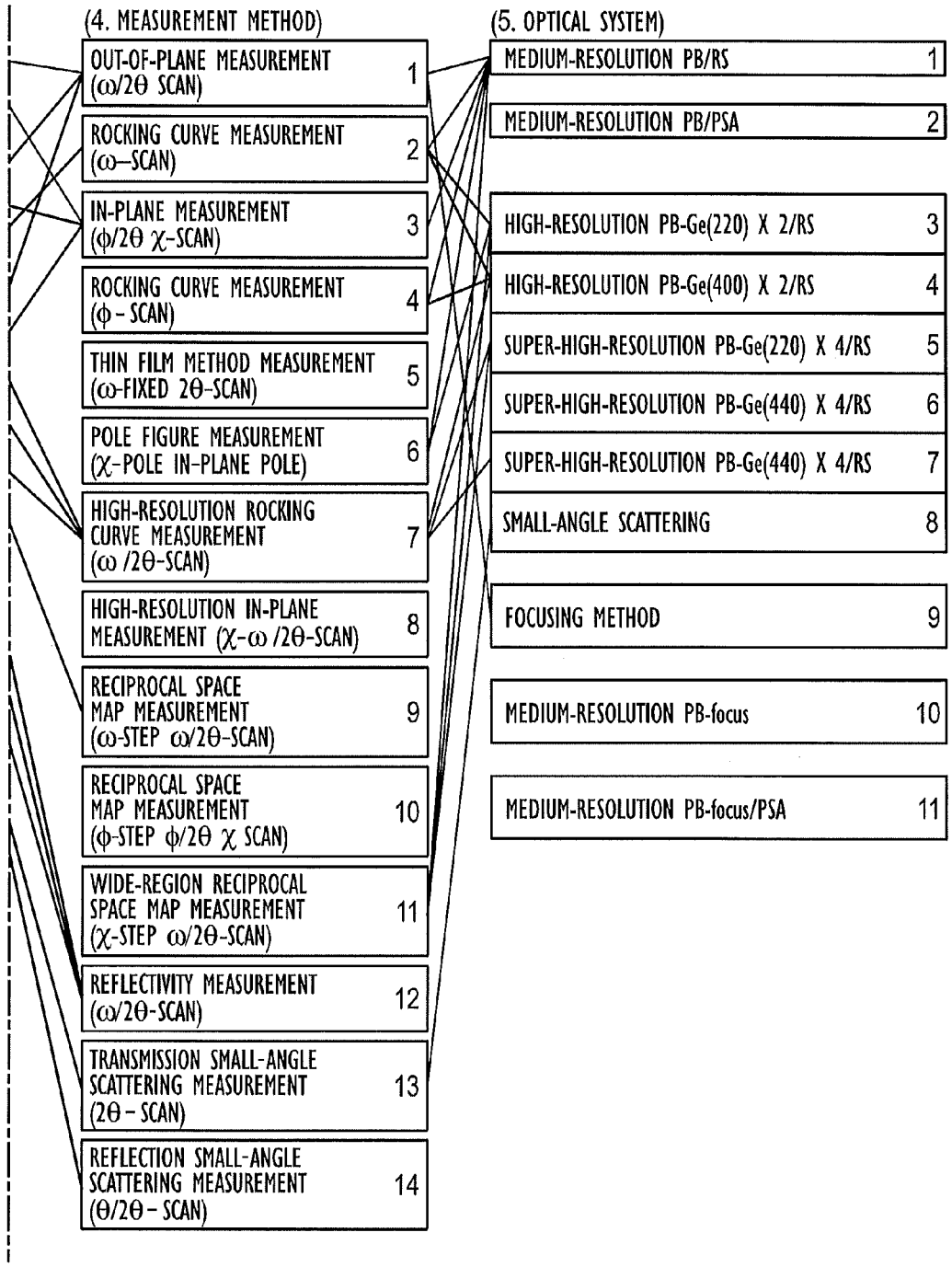

The material evaluation table 38 is a data table, schematically shown in FIG. 5, storing the respective correspondence relationship between the name data for a material to be analyzed, data representing the name of the material field to which the material belongs, data representing the name of the evaluation to be performed on the material (e.g., phase identifications, crystallinity evaluation, lattice strain evaluation, etc.), data representing the name of the measurement method to be performed on the material (e.g., out-of-plane measurement, rocking curve measurement, in-plane measurement, etc.), and data representing the name of the X-ray optical system associated with the measurement method. A detailed description of the material evaluation table 38 will be given further below.

The wizard program 39 functioning as measurement assistance software is program software for assisting the person inputting the measurement conditions, i.e., the user. Specifically, the wizard program 39 is software for implementing functions for issuing advice with regard to the evaluation method when the user inputs the name of the material field or the name of the material regarding the sample to be measured, or issuing advice with regard to the measurement method or the optical system to be used when the user inputs the evaluation method. A detailed description of the wizard program 39 will also be given further below.

The condition file 40 is a memory region for storing measurement conditions inputted by the user or inputted using the wizard program 39. The measurement data file 41 is a memory region for storing data obtained as a result of a measurement. The analysis data file 42 is a memory region for storing, when an analysis process of some sort is performed on the data obtained as a result of a measurement, i.e., measurement data, the post-analysis-process data, i.e., analysis data.

(Material Evaluation Table 38)

The material evaluation table 38 will now be described in detail with reference to the schematic table shown in FIG. 5.

[First Column: Material Field]

In FIG. 5, the first column from the left shows a plurality of items belonging to the category of "material field", which is one type of information relating to a material, arranged vertically. With regard to the items of material fields, semiconductor epitaxial film, semiconductor polycrystal film, semiconductor amorphous film, and other items of material fields are listed. In the items of material fields, a "barrier film" refers to a protective film between each layer in an instance in which the material is multilayer. "Substrate" refers to a single-crystal substrate. "Bulk" refers to a polycrystalline substrate.

[Second Column: Material]

The second column from the left shows a plurality of items belonging to the category of "material", which is another type of information relating to a material, arranged vertically. For the items of material, materials belonging to individual items of the above-mentioned material fields are listed. Lines indicating correspondence relationships are drawn between items of material field and items of material. These lines indicate which materials belong to individual items of material field. For example, it is indicated that materials(ITO, ZnO, CdO, . . . ) listed eleventh from the top from among the items in the second column belong to the material field of "transparent electrode film" listed seventh from the top from among the items listed in the first column.

In other words, the material evaluation table 38 stored in the memory unit 5 in FIG. 1 stores all information indicating which item of material field in column 1 in FIG. 5 each of the items of material in column 2 belongs to.

[Third Column: Evaluation]

The third column from the left shows a plurality of items belonging to the category of "evaluation", arranged vertically. For the items of evaluation, phase identification analysis, crystallinity evaluation, lattice strain evaluation, and other types of items of evaluation are listed. Phase identification analysis is an analysis for finding out what substances are contained in the material. Crystallinity evaluation refers to evaluating the size of crystallites. Orientation evaluation refers to evaluating the preferred orientation samples. Lattice strain evaluation refers to evaluating whether or not a deformation is present in the crystal lattice. Composition evaluation is evaluation of chemical composition (i.e., evaluation of the lattice constant). Lattice constant evaluation refers to evaluating the crystal lattice constant.

"Relaxation degree evaluation" is an evaluation of the following description. In an instance in which a thin film is formed on a substrate, the thin film may be deformed due to the substrate. When the amount of deformation exceeds a certain limit, the deformation is instantaneously relaxed. The relaxation degree is a measure of the extent to which the deformation is relaxed in such an instance.

Of each of the items of "material" in the second column and each of the items of "evaluation" in the third column, those in corresponding relationships with each other are linked by a line. The lines do not link one material to one evaluation, but instead link one material to a plurality of evaluations or one evaluation to a plurality of materials. The drawing shows the eleventh material item from the top of the second column, i.e., "ITO, ZnO, CdO, . . . ", as well as several other material items, linked by straight lines to a plurality of evaluation categories respectively. However, in reality, every one of the material items is linked by straight lines to a plurality of corresponding evaluation categories. However, if these lines are accurately drawn in FIG. 5, the large number of lines linking the second column to the third column will almost completely fill up the space between the second column and the third column, making comprehension difficult. Therefore, in FIG. 5, only the correspondence states between the material item "ITO, ZnO, CdO, . . . ", as well as several other material items, and the evaluation categories in the third column are linked by lines and indicated as representatives.

In other words, the material evaluation table 38 stored in the memory unit 5 in FIG. 1 stores, in relation to all of the material items, which evaluation, from the evaluations listed in the third column, would result in an appropriate evaluation for each of the items of material listed in the second column in FIG. 5.

[Fourth Column: Measurement Method]

The fourth column from the left in FIG. 5 shows a plurality of items belonging to the category of "measurement method," arranged vertically. The individual items of measurement method that are shown, e.g., out-of-plane measurement and the like, have already been described in the description of measurement methods given with reference to FIG. 3; therefore, a description will not be provided here.

Of each of the items of "evaluation" in the third column and each of the items of "measurement method" in the fourth column, those in corresponding relationships with each other are linked by a line. The lines are not limited to those linking one evaluation to one measurement method, and may link one evaluation to a plurality of measurement method or one measurement method to a plurality of evaluations.

FIG. 5 shows, e.g., the first evaluation category, "Phase Identification analysis", from the top in the third column linked to "out-of-plane measurement" at the first place from the top and "in-plane measurement" at the third place from the top of the fourth column. This indicates that Phase Identification analysis can be performed in an appropriate manner if out-of-plane measurement or in-plane measurement is performed.

"Film thickness evaluation" at the eighth place, "roughness evaluation" at the ninth place, and "density evaluation" at the tenth place of the third column are all linked to "reflectivity measurement" at the twelfth place in the fourth column. This indicates that the three entries of film thickness evaluation, roughness evaluation, and density evaluation can be performed in an appropriate manner if reflectivity measurement is performed.

In other words, the material evaluation table 38 stored in the memory unit 5 in FIG. 1 stores, in relation to all of the evaluation categories, which measurement method, from the measurement methods listed in the fourth column, would result in an appropriate evaluation for each of the evaluations listed in the third column in FIG. 5.

[Fifth Column: Optical System]

The fifth column from the left in FIG. 5 (i.e., the rightmost column) shows a plurality of items belonging to the category of "optical system" arranged vertically. The optical systems shown as examples are: (1) medium-resolution PB/RS ("PB" stands for parallel beam and "RS" stands for receiving slit); (2) medium-resolution PB/PSA ("PB" stands for parallel beam and "PSA" stands for receiving slit analyser); (3) high-resolution PB-Ge (220)×2/RS; (4) high-resolution PB-Ge (400)×2/RS; (5) super-high-resolution PB-Ge (220)×4/RS; (6) super-high-resolution PB-Ge (440)×4/RS; (7) small-angle scattering; (8) focusing method; (9) medium-resolution PB-focus; and (10) medium-resolution PB-focus-PSA.

Of each of the items of "measurement method" in the fourth column and each of the items of "optical system" in the fifth column, those in corresponding relationships with each other are linked by a line. The lines are not limited to those linking one measurement method to one optical system, and may link one measurement method to a plurality of optical systems or one optical system to a plurality of measurement methods.

In FIG. 5, e.g., the first measurement method item, "out-of-plane measurement", from the top of the fourth column is linked to "medium-resolution PB/RS" at the first place from the top of the fifth column. This indicates that "out-of-plane measurement" is performed using the "medium-resolution PB/RS" optical system. Also, the sixth measurement method item, "pole figure measurement", is linked to "medium-resolution PB/RS" at the first place and "high-resolution PB-Ge (220)×2/RS" at the third place from the top of the fifth column. This indicates that "pole figure measurement" is performed using the "medium-resolution PB/RS" optical system or the "high-resolution PB-Ge (220)×2/RS" optical system.

Also, the twelfth measurement method item, "reflectivity measurement", in the fourth column is linked to "medium-resolution PB/RS" at the first place, "high-resolution PB-Ge (220)×2/RS" at the third place, and "super-high-resolution PB-Ge (220)×4/RS" at the fifth place from the top of the fifth column. This indicates that "reflectivity measurement" is performed using the "medium-resolution PB/RS" optical system, the "high-resolution PB-Ge (220)×2/RS" optical system, and the "super-high-resolution PB-Ge (220)×4/RS" optical system.

"Small-angle scattering" at the eighth place in the fifth column is an optical system suitable for detecting scattered rays in a small-angle region with regard to the diffraction angle $2\theta$ (e.g., a region of about $2\theta=0°$ to $5°$). "Focusing method" at the ninth place is an optical system suitable for detecting, using a X-ray detector, X-ray that has been emitted by an X-ray source, diffracted by the sample, and focused on a receiving slit.

Displaying lines indicating relationships between the fourth column and the fifth column in relation to all of the items will result in an excessively large number of lines and make comprehension difficult; therefore, FIG. 5 shows only several representative lines.

As can be seen from above, the material evaluation table 38 stored in the memory unit 5 of FIG. 1 stores, in relation to all of the measurement method items, which optical system, from among the optical systems listed in the fifth column, is suitable for accompanying the measurement method listed in the fourth column in FIG. 5.

The data table shown in FIG. 5, i.e., the data table stored in the material evaluation table 38 in the memory unit 5 in FIG. 1 is based on experimentation and experience on the part of the inventor, and has not been arbitrarily defined groundlessly by the inventor. Table 1 shows knowledge obtained as a result of experimentation and experience on the part of the inventor, and the data table in FIG. 5 has been defined on the basis of this knowledge. Table 1 only shows some of the results acquired by the inventor.

Table 1 shows what evaluations are often performed and what measurement methods are often employed in reality in relation to a given material. For example, materials "ITO, ZnO, CdO, . . . " belonging to the material field of "transparent electrode film" are (1) evaluated using orientation analysis evaluation on a frequent basis;

(2) evaluated using each of phase identification analysis evaluation, crystallinity evaluation, lattice strain evaluation, film thickness evaluation/interface evaluation, and density evaluation on a somewhat frequent basis; and (3) evaluated using solid solution composition evaluation and lattice constant evaluation on an occasional basis. The data table shown in FIG. 5 is defined on the basis of knowledge on the part of the inventor of such description.

Also for example, materials "Cu, Al, belonging to the material field of "interconnecting electrode film" are:

(1) evaluated using orientation analysis evaluation on a frequent basis;

(2) evaluated using each of phase identification analysis evaluation, crystallinity evaluation, lattice strain evaluation, film thickness evaluation/interface evaluation, and density evaluation on a somewhat frequent basis; and (3) evaluated using solid solution composition evaluation and lattice constant evaluation on an occasional basis. The data table shown in FIG. 5 is defined on the basis of knowledge on the part of the inventor of such description.

(Wizard Program 39)

The wizard program 39 stored in the memory unit 5 in FIG. 1 is program software for assisting the person performing the analysis, i.e., the user, by means of image-displaying using the display 9, by providing a step-by-step instruction for using the X-ray analysis apparatus 1.

Figure 6:
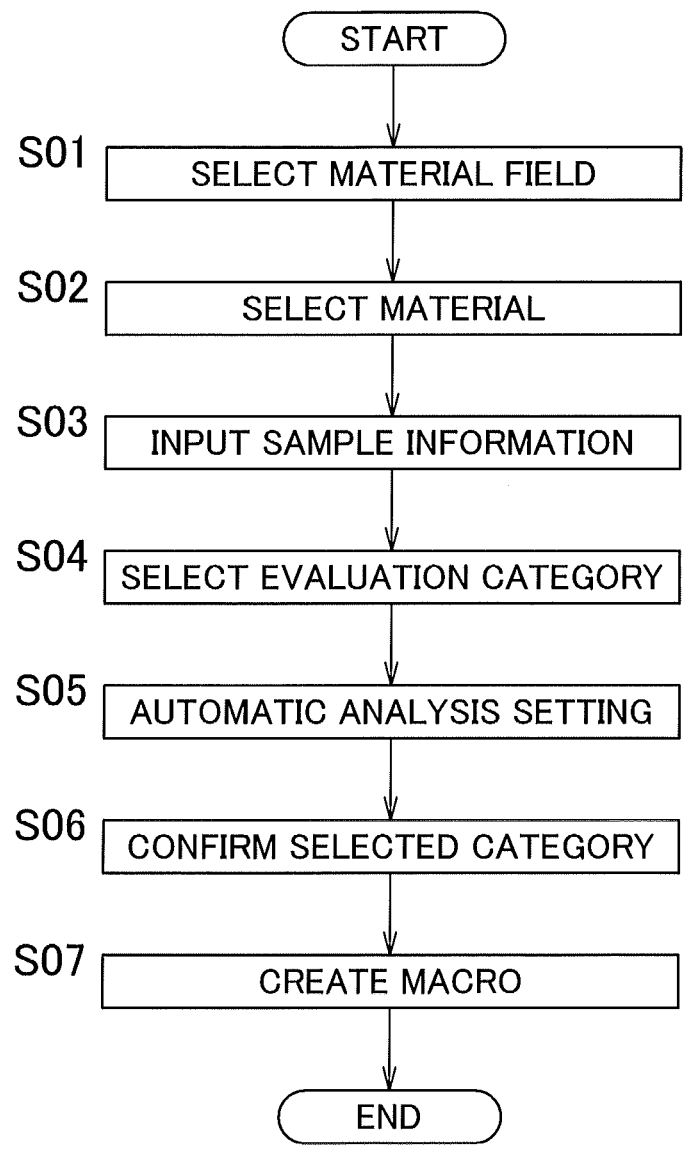
FIG. 6 is a flow chart executed by the wizard program shown in FIG. 1.

Specifically, the wizard program 39 first executes a material field selection routine in step S01 as shown in FIG. 6. In this routine, first, a material field selection screen 45 such as that shown in FIG. 7 is displayed on the screen of the display 9 shown in FIG. 1. This screen displays the items of material field stored in the first column of the data table shown in FIG. 5. The user selects a Selection button 46a corresponding to the desired material field using the mouse 11 shown in FIG. 1. The selected condition is stored in the condition file 40 shown in FIG. 1.

Next, the control proceeds to a material selection routine in step S02. In this routine, a material selection screen 47a such as that shown in FIG. 8 is displayed. This screen displays materials, from the second column in FIG. 5, that belong to the material field selected in FIG. 7. In the drawing, the names of three materials, excluding "other," are displayed. Clicking on "other" results in the names of other materials being displayed in the adjacent window. The user selects, using the mouse 11 shown in FIG. 1, a Selection button 46b corresponding to the desired material. The selected condition is stored in the condition file 40 shown in FIG. 1.

Figure 9:
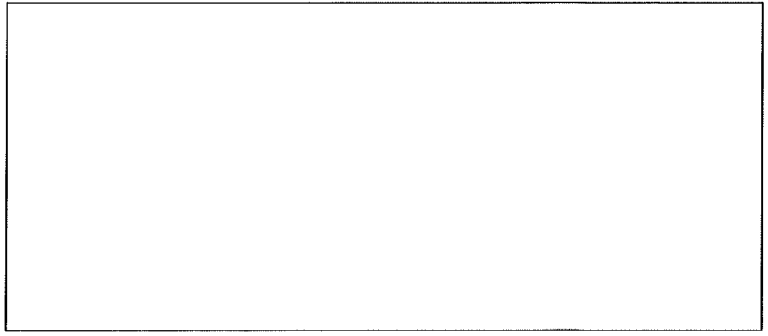
FIG. 9 illustrates a still another example of image display.

In an instance in which, e.g., "Interconnecting film" is selected in the material field selection screen 45 of FIG. 7, a material selection screen 47b such as that shown in FIG. 9 is displayed in the material selection routine. This screen displays materials, from the second column in FIG. 5, that belong to the material field selected in FIG. 7. In FIG. 9, the names of two materials, excluding "other", are displayed. Clicking on "other" results in the names of other materials being displayed in the adjacent window. The user selects, using the mouse 11 shown in FIG. 1, a Selection button 46e corresponding to the desired material. The selected condition is stored in the condition file 40 shown in FIG. 1.

Next, the control proceeds to a sample information input routine in step S03. In this routine, an input screen 48 such as that shown in FIG. 10 is displayed. In accordance with instructions, the user inputs the thickness, width, and height of the sample into predetermined fields 49. The inputted condition data is stored in the condition file 40 shown in FIG. 1.

Next, the control proceeds to an evaluation category selection routine in step S04. In this routine, an evaluation category selection screen 50 such as that shown in FIG. 11 is displayed. This screen displays categories of evaluation stored in the third column of the data table shown in FIG. 5. More specifically, items of evaluation corresponding to the name of material selected in FIG. 8 are displayed. The user selects, using the mouse 11 shown in FIG. 1, a Selection button 46c corresponding to the desired evaluation. The selected condition is stored in the condition file 40 show in FIG. 1.

Figure 12A:
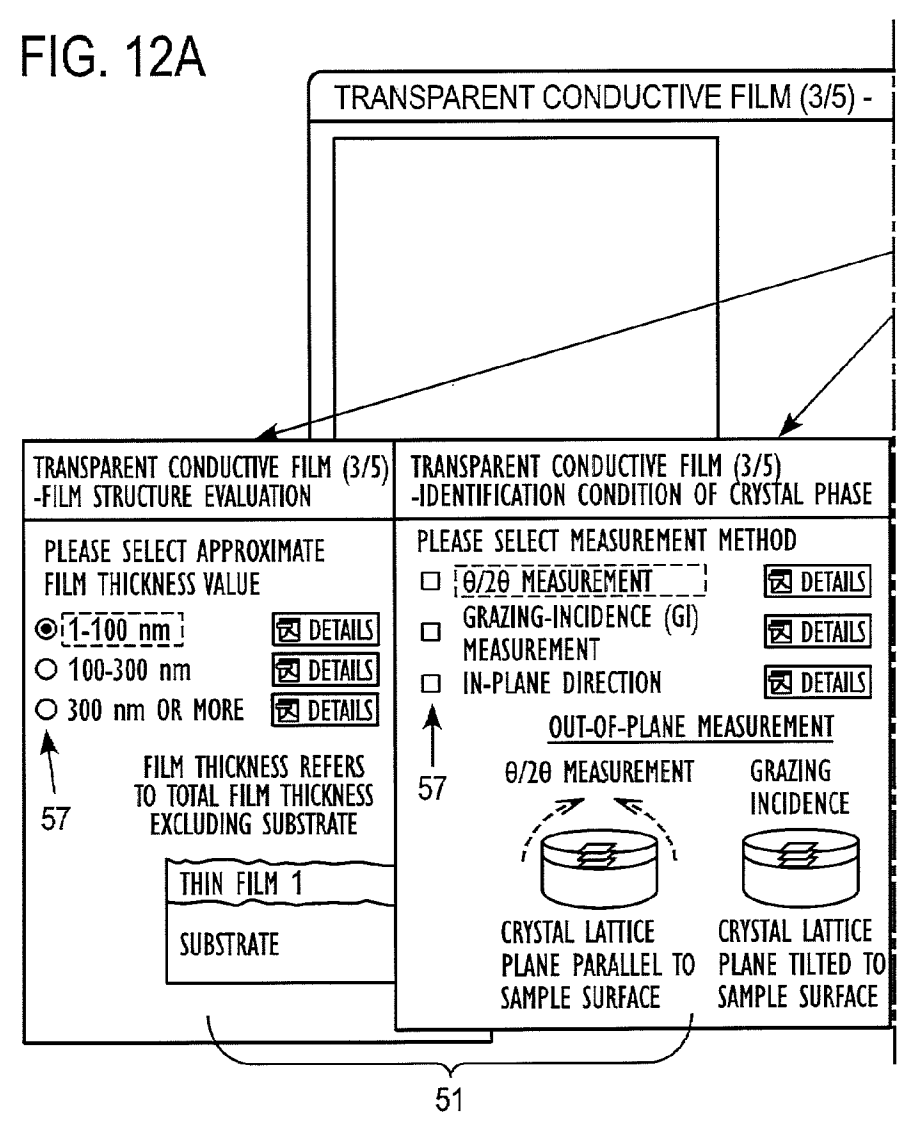
Figure 12B:
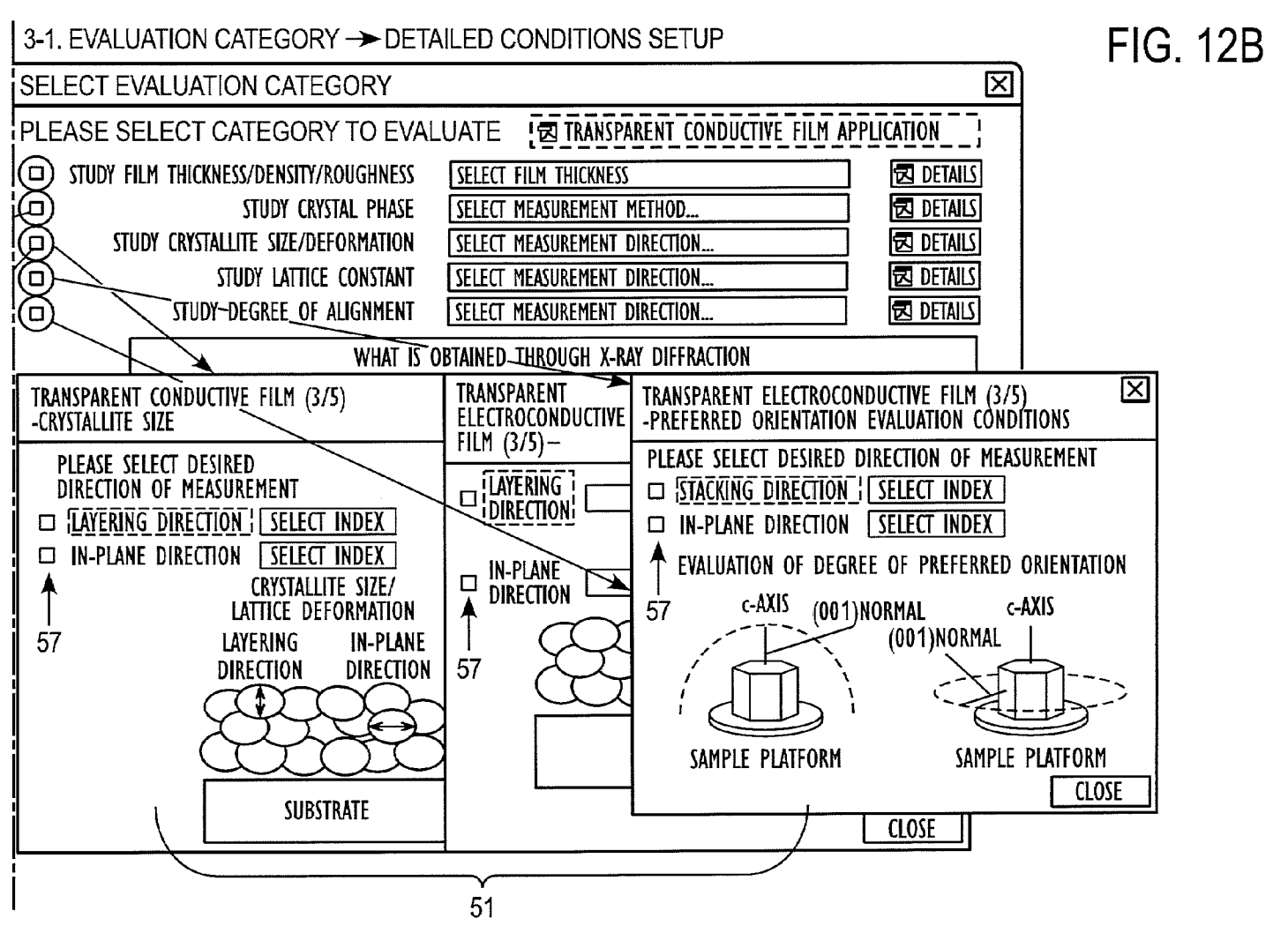

In the present embodiment, when any of the evaluations is checked in FIG. 11, an image 51 for describing the checked evaluation is displayed as a window as shown in FIG. 12. The user can thereby operate the wizard program without making an input error. In this instance, the screen in the image 51 contains a selection screen 57 for selecting a condition that must be specified prior to each of the evaluation processes. The user can input the desired condition through the selection screen 57.

Next, the control proceeds to an automatic analysis setup routine in step S05. In this routine, an automatic analysis setup screen 52 such as that shown in FIG. 13 is displayed. In this display, the evaluation category selected by the user in the evaluation category selection routine in step S04 is displayed. If the user wishes the computer to perform an automatic analysis in relation to the displayed evaluation categories, the user checks a Selection button 46d corresponding to the evaluation category for which the user wishes an automatic analysis to be performed.

Next, the control proceeds to a selected category confirmation routine in step S06. In this routine, a selected category confirmation screen 53 such as that shown in FIG. 14 is displayed. In this screen, measurement conditions selected by the user in the preceding steps are displayed as a list. If the user wishes to amend these measurement conditions, the user can click a Back button 54 to return to the original routines. If the user agrees with the displayed measurement conditions, the user clicks an End button 55a.

In the above control flow, when at least the evaluation category selection routine in step S04 is complete, the computer specifies, in accordance with the program, the names of the required measurement method and optical system from the names of the material field, material, and evaluation selected by the user in FIG. 5.

Figure 16:
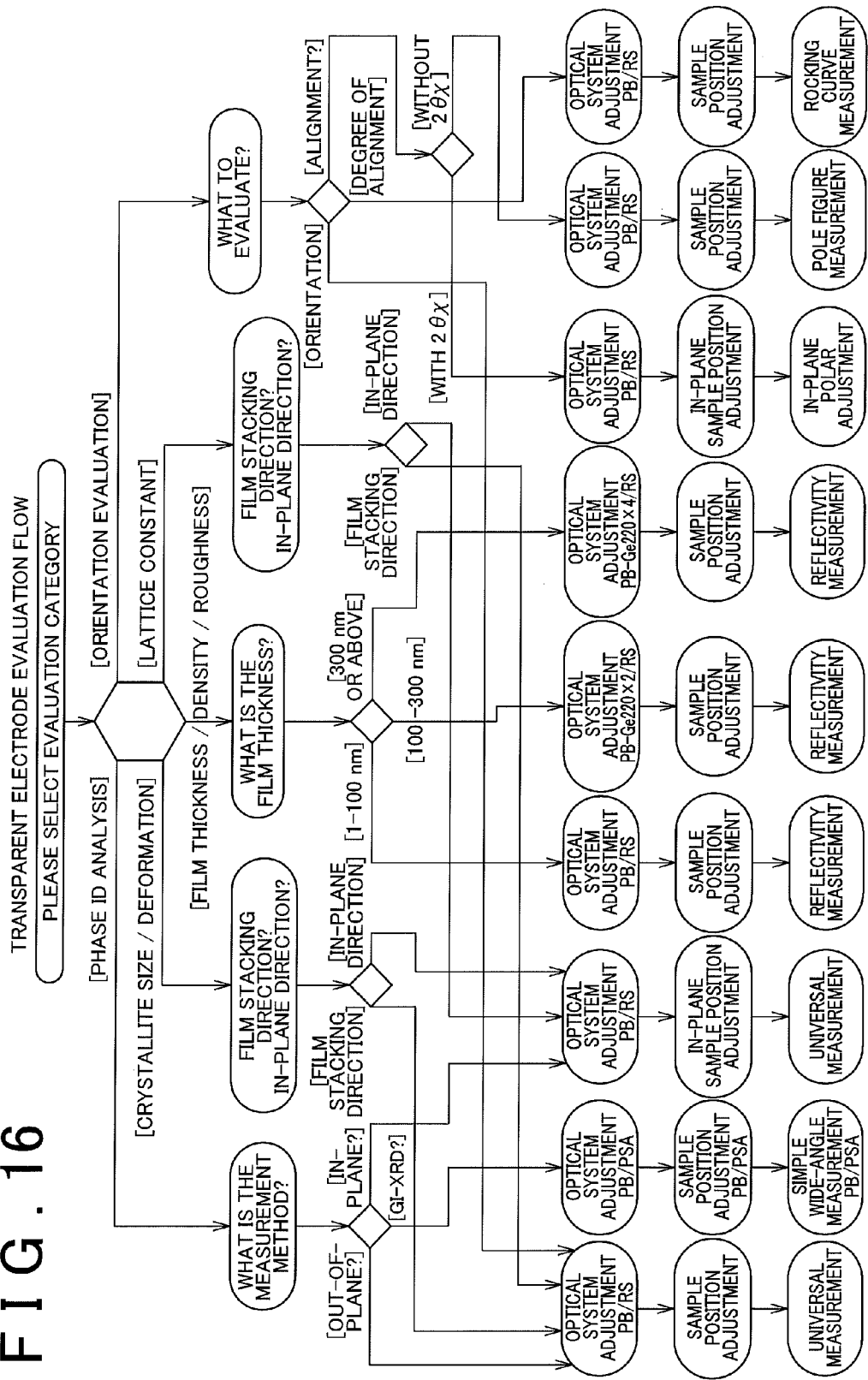

FIG. 16 shows an example of a computation flow for specification of the measurement method and the like of such description. FIG. 16 shows an example of an instance in which a transparent electrode film is selected as a material field and ZnO is selected as a material.

If, e.g., the user chooses phase identification analysis as an evaluation in the evaluation category selection shown in FIG. 11, and chooses out-of-plane measurement as a measurement method in the detailed conditions setup shown in FIG. 12, the computer selects, in accordance with the program, a stage for adjusting the PB/RS optical system, a stage for performing a standard sample position adjustment, and a stage for performing a general out-of-plane measurement.

If, e.g., the user chooses film thickness evaluation as an evaluation in the evaluation category selection shown in FIG. 11, and chooses 100 nm or less in the information input in FIG. 10, the computer selects, in accordance with the program, a stage for adjusting the PB/RS optical system, a stage for performing a normal sample position adjustment, and a stage for performing a reflectivity measurement.

As can be understood from the above description, the X-ray analysis apparatus of the present embodiment is based on the following circumstances regarding conventional X-ray analysis apparatuses.

(1) There is a large variety of material fields that are targeted, as shown, e.g., in the first column of FIG. 5.

(2) In recent X-ray analysis apparatuses, there is an extremely large number of types of evaluations that can be implemented as shown, e.g., in the third column in FIG. 5.

(3) The measurement sequence for each type of evaluation is almost fully established. For example, each of film thickness evaluation, density evaluation, and roughness evaluation is performed according to the following procedure: optical system selection/adjustment→sample position adjustment→reflectivity measurement→reflectivity analysis.

(4) Although a variety of adjustment tools and measurement tools are already available, specific details of adjustment and measurement vary depending on the material and evaluation. Determining the specific details of adjustment and measurement is difficult even for those with experience, and is extremely unfeasible for those without experience.

With such circumstances in view, the following processes are performed in the present embodiment.

(A) The material field and the material (both information relating to the material) are taken as the start of the workflow. The necessary evaluation categories and detailed information are obtained by questioning as required using a wizard format (i.e., by performing questioning at each step), and the measurement flow and the measurement conditions are established.

(B) Specifically, the measurement flow and measurement conditions, which contain a variety of options, are stored in a library (i.e., a data table). With regard to the selected material, information necessary for measurement (e.g., index value or 2θ-value) are acquired from the material database.

A process of such description allows even a user lacking in measurement experience to readily assemble the flow of evaluation categories and the measurement conditions to an optimum state in line with the material being used.

When the End button 55a is clicked in FIG. 14, the control proceeds to a macro creation routine in step S07 shown in FIG. 6. In the macro creation routine, the CPU 2 shown in FIG. 1 defines, as a macro, an instruction regarding the measurement procedure to be transmitted to the X-ray measurement system 8. As well known, a macro is a simple program in which processes comprising a plurality of commands are defined in advance as a single command. When the generation of the macro is complete and the user clicks the End button 55a, the created macro 56 is written in the program. The created macro can be displayed on the screen as indicated by numeral 56 in FIG. 15. The macro will now be described in detail.

(First Embodiment of Measurement Macro)

In basic terms, the CPU 2 creates a macro when the material information shown in FIG. 5 (i.e., "material field" in the first column and "material" in the second column) has been decided, the evaluation (third column) has been decided, and the measurement method (fourth column) and the optical system (fifth column) have been decided.

For example, in an instance in which, in FIG. 5, "phase identification" is selected in "selection of evaluation" in the third column, and "in-plane measurement" is selected in "selection of measurement method" in the fourth column, a macro shown, e.g., in FIG. 17A is created.

In an instance in which "study lattice constant" is selected in "selection of evaluation" in the third column, and "direction within surface plane" is selected in "selection of measurement method" in the fourth column, a macro shown, e.g., in FIG. 17B is created.

In an instance in which "study degree of alignment" is selected in "selection of evaluation" in the third column, and "direction within surface plane" is selected in "selection of measurement method" in the fourth column, a macro shown, e.g., in FIG. 17C is created.

Each of the macros shown in FIGS. 17A, 17B, and 17C comprises four steps indicated by numerals 1 through 4. These steps represent parts (i.e., components) forming the macro; therefore, in the present specifications, these individual steps may be referred to as part steps.

The three instances described above show examples of macros being created in instances in which a single type of evaluation is selected in the selection of evaluation in the third column in FIG. 5. However, selection of evaluation is not limited to one type; a plurality of types of evaluations may be selected. For example, the three types of evaluation shown in FIGS. 17A through 17C may be selected at the same time. In such an instance, if no innovation is made with regard to the course of creating the macro, the three types of macro shown in FIGS. 17A through 17C simply continue from one another. Therefore, the final macro will be one comprising 4×3=12 stages.

Here, the inventor focused on the fact that with regard to the three types of macro shown in FIGS. 17A through 17C, the first through third stages of each of the macros are the same, i.e., are common with each other. This means that in an instance in which the three types of macro shown in FIGS. 17A through 17C are executed in continuation, the process corresponding to the first through third stages of each of the macros do not have to be repeated three times; performing the process once will suffice.

Figure 18:
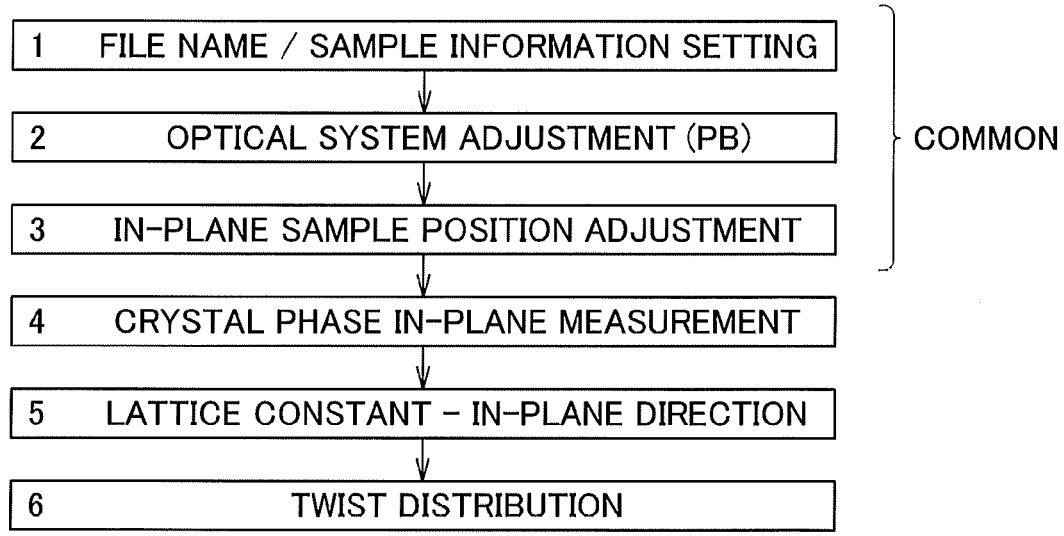
FIG. 18 illustrates another example of a macro.

A setup in which stages (part steps) that are common between the macros are performed only once results in the overall macro being in a state shown in FIG. 18. This macro results in the desired common steps 1 through 3 being executed without the steps being repeated unnecessarily. It is thereby possible to implement the three measurement methods corresponding to the three macros shown in FIGS. 17A through 17C without burdening the user in terms of workload and without greatly burdening the flow of control in the macro.

In the above description, the identical part steps 1 through 3 are executed once only. However, what is required is only that the execution of the identical part steps 1 through 3 is prevented from being repeated by an amount corresponding to the three measurement methods (i.e., three times). Therefore, the burden on the user or the like can still be reduced if the identical part steps 1 through 3 are performed twice. In other words, the common part steps 1 through 3 need only be executed at least one.

The macro shown in FIG. 18 can be performed with a total of six stages (part steps). A setup of such description, in which the common stages are executed once only, makes it possible to reduce the workload as well as cut the processing time.

(Second Embodiment of Measurement Macro)

Figure 19A:
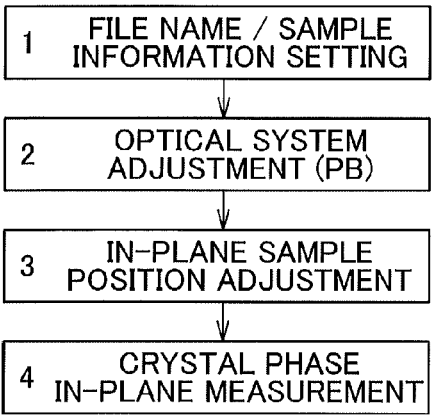
FIGS. 19A, 19B and 19C illustrate other examples of a macro.
Figure 19B:
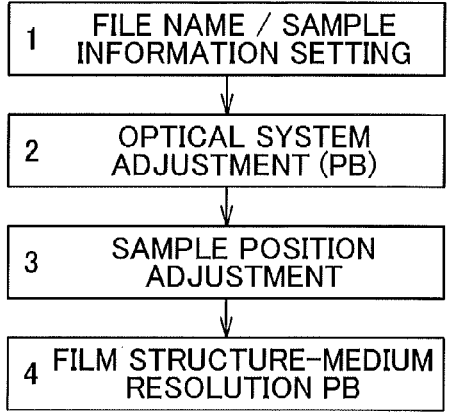
Figure 19C:
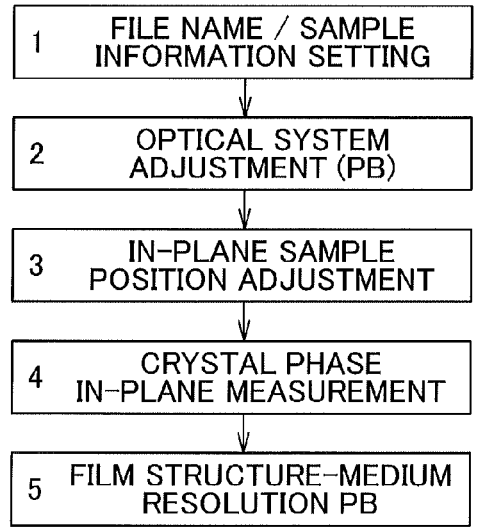

FIGS. 19A through 19C show another embodiment relating to the creation of a macro. This embodiment is one in which two types of evaluation shown in FIGS. 19A and 19B are selected at the same time. In this instance, the two types of macro have stages 1 and 2 (part steps 1 and 2) in common with each other, and the common stages can be shared.

Looking at stage 3 (part step 3) of these macros, the corresponding stages differ; therefore, it can be thought, in basic terms, that the stages cannot be shared. However, stage 3 of macro (a) is "in-plane sample position adjustment" and stage 3 of macro (b) is "sample position adjustment." In this instance, with regard to adjustment accuracy, it is necessary to set the accuracy of the in-plane sample position adjustment so as to be higher than the accuracy of the sample position adjustment. This means that once the in-plane sample position adjustment has been performed, the positional accuracy is sufficiently high even without performing the sample position adjustment of stage 3 in macro (b).

In other words, the function of stage 3 for in-plane sample position adjustment, which is a part step included in the first macro, encompasses the function of stage 3 for sample position adjustment, which is a part step included in the second macro; i.e., the function of stage 3 of the first macro is a wider-ranging, or a higher, function than the function of stage 3 of the second macro.

Therefore, in the present embodiment, as shown in FIG. 19C, in the final macro, stages 1 and 2 are shared, and with regard to the sample position adjustment in stage 3, only the highly accurate in-plane sample position adjustment is executed, once. Whereas if the two types of macro are performed separately it is necessary to follow eight stages (part steps), according to the present embodiment, stages 1 and 2 are shared, and only the more accurate one of the stages is executed for stage 3, and the number of stages can be kept to 5. Therefore, compared to an instance in which the two types of macro are executed separately, it is possible to reduce the burden on the user in terms of workload and cut the processing time.

As described above, in the present embodiment, in an instance in which a plurality of evaluations are selected, an innovation is made to the macros, whereby the measurement flow is optimized so that measurement is possible with minimal workload (i.e., with minimal time, component replacement, and the like). Specifically, based on the type of evaluation and detailed information selected, stages that are common between a plurality of measurement methods are shared between the measurement methods by implementing the stages once. If there are a plurality of necessary optical systems, allocating is performed according to categories that can be measured using each of the optical systems. A process of such description allows even a user lacking in measurement experience to readily assemble the flow of evaluation categories and measurement conditions to an optimum state in line with the material being used.

(Execution of X-Ray Measurement)

When the measurement method shown in FIG. 5 (see the fourth column) and an associated optical system (see the fifth column) have been decided as described above, corresponding information is transmitted to the measurement software 37 shown in FIG. 1, and the measurement software 37 transmits, to the X-ray measurement system 8, information for implementing the designated measurement method. The X-ray measurement system 8 thereby implements the designated measurement method according to the designated conditions, and as a result, measurement data desired by the user is obtained.

As can be understood from the above description, according to the present embodiment, merely inputting the name of the material field and the name of the material makes it possible for anyone to establish, in a simple and accurate manner, the evaluation method (e.g., phase identification analysis, crystallinity evaluation, and the like) suited to the material and a measurement method suited to the material.

In particular, in the present embodiment, the name of the evaluation is selected on the basis of both the name of the material field and the name of the material, therefore making it possible to specify an appropriate measurement method for the material.

(Other Embodiments)

The present invention has been described above with reference to preferred embodiments. However, the present invention is not limited to the embodiments, and can be modified in a variety of manners within the scope of the invention set forth in the claims.

For example, the X-ray measurement system 8 is not limited to that configured as shown in FIG. 2. The X-ray measurement system 8 may have another configuration of choice as long as the X-ray measurement system has a function enabling a plurality of measurement methods to be implemented.

DESCRIPTION OF REFERENCE SYMBOLS

1.X-ray analysis apparatus, 2.CPU(arithmetic control method), 3.ROM, 4.RAM, 5.memory unit, 8.X-ray measurement system, 9.display(image display means), 10.keyboard(input means), 11. mouse(input means), 12.data bus, 15.goniometer(angle-measuring instrument), 16.X-ray generation device, 17.X-ray detector, 18.filament, 19.target, 22.incident optical system, 23.receiving optical system, 24.cross-beam optics (CBO) unit, 25.monochromator unit, 26.incident optical unit, 27.incident slit box, 30.first receiving slit box, 31.first receiving optical unit, 32.second receiving optical unit, 33.second receiving slit box, 34.attenuator unit, 37.measurement software, 38.material evaluation table, 39.wizard program, 40.condition file, 41.measurement data file, 42.analysis data file, 45.material field selection screen, 46a,46b,46c,46d,46e.Selection button, 47a,47b.material selection screen, 48.input screen, 49.predetermined fields, 50.evaluation category selection screen, 51.image for describing the checked evaluation, 52.automatic analysis setup screen, 53.selected category confirmation screen, 54.Back button, 55a.End button, 56.macro, F.X-ray focus, R1.incident X-ray, R2.diffracted X-ray, S.sample, θ.incident angle, 2θ.diffraction angle.

TABLE 1

| | | | ← poly crystalline X-ray diffraction measurement single crystalline → | | | | | | |
|---|---|---|---|---|---|---|---|---|---|
| | Class | Major material | Phase ID | crystallite size | orientation | lattece strain | composition (solid solution) | lattice constant, crystallinity | relaxation |
| Semi- conductor epitaxial film | IV-IV compound | Si, SiGe, SiC ... | — | — | Δ | — | ⊚ | ⊚ | ⊚ |
| | III-V compound | GaAs, AlGaAs, InP ... | — | — | Δ | — | ⊚ | ⊚ | ⊚ |
| | III-N compound | GaN, AlN, InN, BN ... | Δ | — | ○ | Δ | ⊚ | ⊚ | ⊚ |
| | II-VI compound | ZnO, ZnSe ... | Δ | — | ○ | Δ | Δ | ○ | ○ |
| | others | FeSi$_2$ ... | Δ | Δ | ⊚ | Δ | Δ | Δ | Δ |
| semiconductor poly-film | | poly-Si, μc-Si ... | — | ○ | ⊚ | ○ | — | ○ | — |

TABLE 1-continued

| Class | | Major material | | | | | | | |
|---|---|---|---|---|---|---|---|---|---|
| semiconductor amourphous film | | a-Si, a-SiN... | — | Δ | — | Δ | ○ | — | — |
| barrier film | | Ta, TaN, Ti, SiN,... | ○ | ○ | Δ | ○ | ⊚ | Δ | — |
| electrode -interconnect- | | Cu, Al... | Δ | ○ | ⊚ | ○ | Δ | Δ | — |
| electrode | cotact | CoSi$_2$, NiSi, W, Pt, Ir... | ⊚ | ○ | ⊚ | ○ | Δ | Δ | Δ |
| | TCO | ITO, ZnO, CdO... | ○ | ○ | ⊚ | ○ | Δ | Δ | — |
| low-k | | | — | — | — | — | — | — | — |
| high-k | | ZrO$_2$, HfAlOx, SiON... | ⊚ | ○ | Δ | ○ | ○ | — | — |
| Ferroelectric film | | PZT, SBT, BST, AlN... | ⊚ | Δ | ⊚ | ○ | ⊚ | Δ | Δ |
| coating film | | DLC... | — | — | — | Δ | Δ | — | — |
| organic film | | small molecular material, polymers. | ○ | ○ | ○ | Δ | — | Δ | — |
| magnetic film | media | Co, CoCrPt... | ○ | ○ | ○ | ○ | Δ | ○ | — |
| | next generation | FePt, CoPt, granular... | ○ | ○ | ⊚ | ○ | Δ | ○ | — |
| | head | NiFe/Ta... | ○ | ○ | Δ | ○ | ○ | Δ | — |
| | others | MnGaAs, Fe-epi... | Δ | ○ | ⊚ | ○ | ○ | ○ | ○ |
| piezoelectric material | | LN, LT, SiO$_2$, Langasite, AlN, BBO... | Δ | — | ○ | ○ | ○ | ⊚ | — |
| super conductor | | YBCO, La2CuO4, MgB2... | ○ | ○ | ⊚ | ○ | ○ | ○ | ○ |
| substrate | | Si, GaAs, Sap, SiC, ZnO, YSZ, STO, LSAT... | Δ | — | Δ | ○ | Δ | ⊚ | — |
| bulk | | composite subst (ITO/Gl), UV window (CaF2, BaF2) | Δ | Δ | ○ | — | — | — | — |
| nano material | | nano particle, phonic material, mesoporous material | — | Δ | Δ | Δ | — | ○ | — |

| | | | Reflectivity measurement | | Small angle scattering pore/particle size |
|---|---|---|---|---|---|
| Class | | Major material | thickness, roughness | density | distribution |
| Semiconductor epitaxial film | IV-IV compound | Si, SiGe, SiC... | ⊚ | ○ | — |
| | III-V compound | GaAs, AlGaAs, InP... | ⊚ | ○ | — |
| | III-N compound | GaN, AlN, InN, BN... | ⊚ | ○ | — |
| | II-VI compound | ZnO, ZnSe... | Δ | Δ | — |
| | others | FeSi$_2$... | Δ | Δ | — |
| semiconductor poly-film | | poly-Si, μc-Si... | ⊚ | ⊚ | — |
| semiconductor amourphous film | | a-Si, a-SiN... | ⊚ | ⊚ | — |
| barrier film | | Ta, TaN, Ti, SiN,... | ○ | ○ | — |
| electrode -interconnect- | | Cu, Al... | ○ | ○ | — |
| electrode | cotact | CoSi$_2$, NiSi, W, Pt, Ir... | ○ | ○ | — |
| | TCO | ITO, ZnO, CdO... | ○ | ○ | — |
| low-k | | | ⊚ | ⊚ | ⊚ |
| high-k | | ZrO$_2$, HfAlOx, SiON... | ⊚ | ⊚ | — |
| Ferroelectric film | | PZT, SBT, BST, AlN... | ○ | ○ | — |
| coating film | | DLC... | ⊚ | ⊚ | — |
| organic film | | small molecular material, polymers. | ○ | ○ | — |
| magnetic film | media | Co, CoCrPt... | ⊚ | ○ | — |
| | next generation | FePt, CoPt, granular... | ○ | ○ | ⊚ |
| | head | NiFe/Ta... | ⊚ | ⊚ | — |
| | others | MnGaAs, Fe-epi... | ⊚ | ⊚ | — |
| piezoelectric material | | LN, LT, SiO$_2$, Langasite, AlN, BBO... | Δ | ○ | — |
| super conductor | | YBCO, La2CuO4, MgB2... | Δ | Δ | — |
| substrate | | Si, GaAs, Sap, SiC, ZnO, YSZ, STO, LSAT... | Δ | — | — |
| bulk | | composite subst (ITO/Gl), UV window (CaF2, BaF2) | Δ | Δ | — |
| nano material | | nano particle, phonic material, mesoporous material | ○ | ○ | ⊚ |

Legend symbols: ⊚ Frequently evaluated, ○ often evaluated, Δ occasionally evaluated, — seldom evaluated

What is claimed is:

1. An X-ray analysis apparatus having a function for enabling a plurality of measurement methods to be implemented, the X-ray analysis apparatus having:
   a measurement system configured to implement a plurality of measurement methods;
   measurement software for implementing, in a selective manner, each of the measurement methods;
   memory means for storing information relating to a material to be measured, and at least one evaluation type identifier identifying of an evaluation suitable to be performed on the material;
   input means for inputting the information relating to the material;
   evaluation type computation means for performing a computation for selecting the at least one evaluation type identifier identifying an evaluation suitable to be performed on the material, wherein the computation is performed on the basis of the information relating to the material inputted using the input means; and
   measurement method selection means for selecting a corresponding measurement method on the basis of the selected at least one evaluation type identifier.

2. The X-ray analysis apparatus according to claim 1, wherein the information relating to the material includes a name of a material field.

3. The X-ray analysis apparatus according to claim 1, wherein the information relating to the material includes a name of the material.

4. The X-ray analysis apparatus according to claim 1, wherein the information relating to the material includes a name of a material field and a name of the material.

5. The X-ray analysis apparatus according to claim 1, having:
- memory means for storing the configuration of a plurality of types of optical system; and
- optical system computation means for performing computation in which an appropriate optical system configuration is selected from the plurality of types of optical system on the basis of a combination of the at least one evaluation type identifier and the measurement method.

6. The X-ray analysis apparatus according to claim 5 having input means for inputting the size of the material,
- wherein the optical system computation means uses the inputted size of the material as a determining material for the computation for selecting the configuration of the optical system.

7. The X-ray analysis apparatus according to claim 1, having:
- macro creation means for creating a macro for implementing the measurement methods;
- wherein the macro creation means is capable of creating a macro, comprising a plurality of part steps, for implementing each of the plurality of measurement methods; and
- in an instance in which at least two of the plurality of measurement methods are being implemented, and macros corresponding to each of the measurement methods include identical part steps, the macro creation means creates a macro in which execution of at least one of the identical part steps is omitted and part steps that differ between each of the measurement methods are sequentially executed.

8. The X-ray analysis apparatus according to claim 1, having macro creation means for creating a macro for implementing the measurement methods;
- wherein the macro creation means is capable of creating a macro for implementing a macro, comprising a plurality of part steps, for implementing each of the plurality of measurement methods; and
- in an instance in which at least two of the plurality of measurement methods are being implemented, and a function of a part step included in a first macro, which is one of the macros corresponding to each of the measurement methods, encompasses a function of a part step included in a second macro, which is another macro, the macro creation means creates a macro in which the part step belonging to the first macro is used while the part step belonging to the second macro is not used, and part steps that differ between each of the measurement methods are sequentially executed.

9. The X-ray analysis apparatus according to claim 1, wherein the memory means is configured to store (i) information relating to a plurality of materials and (ii) evaluation information, wherein the evaluation information comprises a plurality of evaluation type identifiers identifying types of evaluations suitable to be performed on the plurality of materials.

* * * * *